US008524380B2

(12) United States Patent
Kim et al.

(10) Patent No.: US 8,524,380 B2
(45) Date of Patent: Sep. 3, 2013

(54) HETEROCYCLIC COMPOUND AND ORGANIC LIGHT-EMITTING DEVICE INCLUDING THE SAME

(75) Inventors: Young-Kook Kim, Yongin (KR); Seok-Hwan Hwang, Yongin (KR); Yoon-Hyun Kwak, Yongin (KR); Hye-Jin Jung, Yongin (KR); Jong-Hyuk Lee, Yongin (KR); Jin-O Lim, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 363 days.

(21) Appl. No.: 12/860,817

(22) Filed: Aug. 20, 2010

(65) Prior Publication Data

US 2011/0049490 A1    Mar. 3, 2011

(30) Foreign Application Priority Data

Sep. 3, 2009  (KR) .................. 10-2009-0083154

(51) Int. Cl.
*H01L 51/54* (2006.01)
*C07D 209/58* (2006.01)

(52) U.S. Cl.
USPC ........... 428/690; 548/418; 548/305.1; 585/27

(58) Field of Classification Search
None
See application file for complete search history.

(56) References Cited

U.S. PATENT DOCUMENTS

| | | | |
|---|---|---|---|
| 6,465,115 B2 | 10/2002 | Shi et al. | |
| 6,596,415 B2 | 7/2003 | Shi et al. | |
| 7,051,949 B2 | 5/2006 | Aiyama | |
| 7,700,201 B2 | 4/2010 | Seo et al. | |
| 7,714,323 B2 | 5/2010 | Hwang et al. | |
| 7,745,819 B2 | 6/2010 | Lee et al. | |
| 2005/0045887 A1* | 3/2005 | Kang et al. | 257/66 |
| 2007/0009758 A1 | 1/2007 | Funahashi | |
| 2007/0069203 A1* | 3/2007 | Lee et al. | 257/40 |
| 2007/0176163 A1 | 8/2007 | Drolet et al. | |
| 2008/0203905 A1 | 8/2008 | Je et al. | |
| 2009/0058289 A1* | 3/2009 | Stoessel et al. | 313/504 |

FOREIGN PATENT DOCUMENTS

| | | |
|---|---|---|
| JP | 2008-078362 A | 4/2008 |
| KR | 10-2004-0057862 A | 7/2004 |
| KR | 10-2005-0107809 A | 11/2005 |
| KR | 10-2007-0003586 A | 1/2007 |

OTHER PUBLICATIONS

KIPO Registration Determination Certificate dated Sep. 27, 2012, for Korean priority Patent application 10-2009-0083154, (5 pages).

* cited by examiner

*Primary Examiner* — Gerard Higgins
*Assistant Examiner* — J. L. Yang
(74) *Attorney, Agent, or Firm* — Christie, Parker & Hale, LLP

(57) ABSTRACT

Embodiments of the present invention are directed to heterocyclic compounds and organic light-emitting devices including the heterocyclic compounds. The organic light-emitting devices using the heterocyclic compounds have high-efficiency, low driving voltages, high luminance and long lifespans.

21 Claims, 1 Drawing Sheet

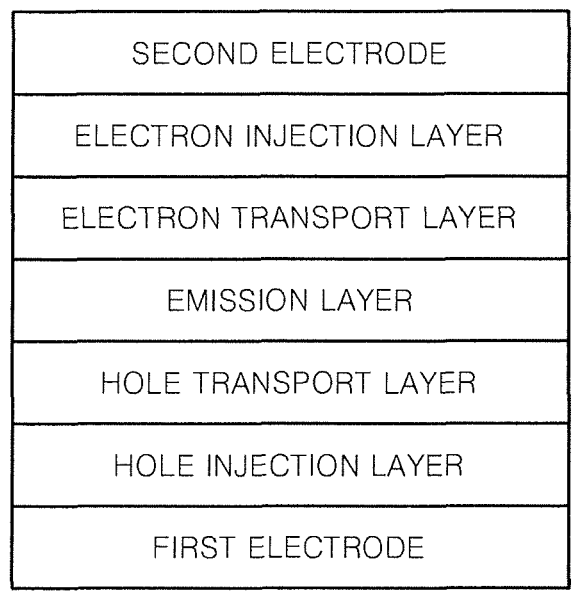

HETEROCYCLIC COMPOUND AND ORGANIC LIGHT-EMITTING DEVICE INCLUDING THE SAME

CROSS-REFERENCE TO RELATED PATENT APPLICATION

This application claims priority to and the benefit of Korean Patent Application No. 10-2009-0083154, filed on Sep. 3, 2009 in the Korean Intellectual Property Office, the entire content of which is incorporated herein by reference.

BACKGROUND OF THE INVENTION

1. Field of the Invention

The present invention relates to heterocyclic compounds and organic light-emitting devices including the heterocyclic compounds.

2. Description of the Related Art

Organic light-emitting devices are self-emission type display devices, and have wide viewing angles, high contrast ratios, and short response times. Due to these characteristics, organic light-emitting devices are drawing much attention.

Light-emitting devices can be categorized into inorganic light-emitting devices which include emission layers containing inorganic compounds, and organic light-emitting devices which include containing organic compounds. Research has been actively conducted into organic light-emitting devices, since organic light-emitting devices have higher luminance, lower driving voltages, and shorter response times than inorganic light-emitting devices, and organic light-emitting devices can produce more colors than inorganic light emitting devices.

Typically, an organic light-emitting device has a stack structure including an anode, a cathode and an organic emission layer therebetween. However, a hole injection layer and/or a hole transport layer may be further stacked between the anode and the organic emission layer, and/or an electron transport layer may be further stacked between the organic emission layer and the cathode. In other words, an organic light-emitting device may have an anode/hole transport layer/organic emission layer/cathode stack structure, or an anode/hole transport layer/organic emission layer/electron transport layer/cathode stack structure.

Organic light-emitting devices including known light-emitting materials do not have satisfactory life span, luminescence efficiency, or power consumption characteristics, thus leaving much room for improvement.

SUMMARY OF THE INVENTION

According to embodiments of the present invention, an organic layer material has improved electrical stability and charge transport capabilities, high glass transition temperature, and improved ability to prevent crystallization. The organic layer material is suitable for fluorescent or phosphorescent organic light-emitting devices (OLEDs) which can realize all colors, including red, green, blue, and white.

In some embodiments of the present invention, a method of preparing the organic layer material is provided.

In other embodiments of the present invention, an organic light-emitting device includes an organic layer including the organic layer material.

In yet other embodiments of the present invention, a flat panel display device includes the organic light-emitting device.

According to embodiments of the present invention, a heterocyclic compound includes a compound represented by Formula 1 below:

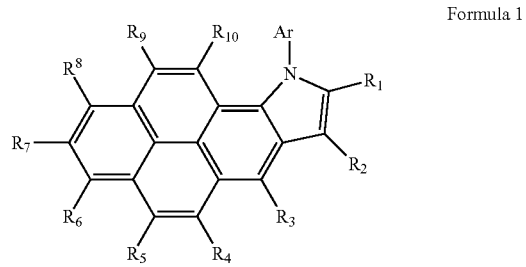

Formula 1

In Formula 1, Ar may be selected from substituted and unsubstituted $C_6$-$C_{60}$ aryl groups, substituted and unsubstituted $C_4$-$C_{60}$ heteroaryl groups, amino groups substituted with at least one substituted or unsubstituted $C_5$-$C_{50}$ aryl group, and substituted and unsubstituted $C_6$-$C_{60}$ condensed polycyclic groups. Each of $R_1$ through $R_{10}$ may be independently selected from hydrogen atoms, heavy hydrogen atoms, substituted and unsubstituted $C_1$-$C_{50}$ alkyl groups, substituted and unsubstituted $C_1$-$C_{50}$ alkoxy groups, substituted and unsubstituted $C_1$-$C_{50}$ alkoxycarbonyl groups, substituted and unsubstituted $C_6$-$C_{60}$ aryl groups, substituted and unsubstituted $C_5$-$C_{50}$ aryloxy groups, substituted and unsubstituted $C_5$-$C_{50}$ arylthio groups, amino groups substituted with at least one substituted or unsubstituted $C_5$-$C_{50}$ aryl group, substituted and unsubstituted $C_3$-$C_{50}$ carbon rings, substituted and unsubstituted $C_4$-$C_{60}$ heteroaryl groups, substituted and unsubstituted $C_4$-$C_{60}$ heterocyclic groups, substituted and unsubstituted $C_6$-$C_{60}$ condensed polycyclic groups, halogen atoms, cyano groups, hydroxyl groups, and carboxyl groups.

According to other embodiments of the present invention, an organic light-emitting device includes a first electrode, a second electrode, and an organic layer between the first and second electrodes. The organic layer includes at least one organic layer having the heterocyclic compound.

According to yet other embodiments of the present invention, a flat panel display device includes the organic light-emitting device, and the first electrode of the organic light-emitting device is electrically connected to a source electrode or a drain electrode of a thin film transistor.

According to other embodiments of the present invention, an organic light-emitting device includes a first electrode, a second electrode, and an organic layer between the first electrode and the second electrode. The organic layer includes at least one layer comprising the heterocyclic compound, which layer can be formed using a wet process.

The at least one layer included in the organic light-emitting device may be formed using the heterocyclic compound and according to a wet process.

BRIEF DESCRIPTION OF THE DRAWING

The above and other features and advantages of the present invention will become more apparent by reference to the following detailed description when considered in conjunction with the attached drawing in which:

FIG. 1 is a schematic diagram depicting the structure of an organic light-emitting device according to an embodiment of the present invention.

DETAILED DESCRIPTION OF THE INVENTION

According to some embodiments of the present invention, a heterocyclic compound is represented by Formula 1 below, and the heterocyclic compound may be used to form an organic layer of an organic light-emitting device (OLED).

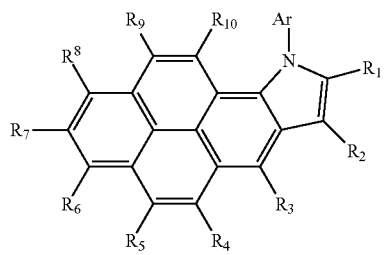

Formula 1

In Formula 1, Ar may be selected from substituted and unsubstituted $C_6$-$C_{60}$ aryl groups, substituted and unsubstituted $C_4$-$C_{60}$ heteroaryl groups, amino groups substituted with at least one substituted or unsubstituted $C_5$-$C_{50}$ aryl group, and substituted and unsubstituted $C_6$-$C_{60}$ condensed polycyclic groups. Each of $R_1$ through $R_{10}$ may be independently selected from hydrogen atoms, heavy hydrogen atoms, substituted and unsubstituted $C_1$-$C_{50}$ alkyl groups, substituted and unsubstituted $C_1$-$C_{50}$ alkoxy groups, substituted and unsubstituted $C_1$-$C_{50}$ alkoxycarbonyl groups, substituted and unsubstituted $C_6$-$C_{60}$ aryl groups, substituted and unsubstituted $C_5$-$C_{50}$ aryloxy groups, substituted and unsubstituted $C_5$-$C_{50}$ arylthio groups, amino groups substituted with at least one substituted or unsubstituted $C_5$-$C_{50}$ aryl group, substituted and unsubstituted $C_3$-$C_{50}$ carbon rings, substituted and unsubstituted $C_4$-$C_{60}$ heteroaryl groups, substituted and unsubstituted $C_4$-$C_{60}$ heterocyclic groups, substituted and unsubstituted $C_6$-$C_{60}$ condensed polycyclic groups, halogen atoms, cyano groups, hydroxyl groups, and carboxyl groups.

In Formula 1, Ar may be selected from substituted and unsubstituted $C_6$-$C_{60}$ aryl groups (for example, aryl groups having from 6 to 18 carbon atoms in the aromatic ring), and substituted and unsubstituted $C_4$-$C_{60}$ heteroaryl groups (for example, heteroaryl groups having from 5 to 20 carbon atoms in the aromatic ring).

Nonlimiting examples of the aryl group represented by Ar include phenyl groups, 1-naphthyl groups, 2-naphthyl groups, 1-anthracenyl groups, 2-anthracenyl groups, 9-anthracenyl groups, 1-phenanthryl groups, 2-phenanthryl groups, 3-phenanthryl groups, 4-phenanthryl groups, 9-phenanthryl groups, 1-naphthacenyl groups, 2-naphthacenyl groups, 9-naphthacenyl groups, 1-pyrenyl groups, 2-pyrenyl groups, 4-pyrenyl groups, 2-biphenyl groups, 3-biphenyl groups, 4-biphenyl groups, p-terphenyl-4-yl groups, p-terphenyl-3-yl groups, p-terphenyl-2-yl groups, m-terphenyl-4-yl groups, m-terphenyl-3-yl groups, and m-terphenyl-2-yl groups.

Nonlimiting examples of the heteroaryl group represented by Ar include thiophenyl groups, 1-phenylthiophenyl groups, 1,4-diphenylthiophenyl groups, benzothiophenyl groups, 1-phenylbenzothiophenyl groups, 1,8-diphenylbenzothiophenyl groups, furyl groups, 1-phenyldibenzothiophenyl groups, 1,8-diphenylthiophenyl groups, dibenzofuranyl groups, 1-phenyldibenzofuranyl groups, 1,8-diphenyldibenzofuranyl groups, and benzothiazolyl groups.

Nonlimiting examples of the aryloxy group represented by $R_1$ through $R_{10}$ include phenyloxy groups, 1-naphthyloxy groups, 2-naphthyloxy groups, 4-biphenyloxy groups, p-terphenyl-4-yloxy groups, and p-tolyloxy groups. For example, the aryloxy group may be a phenyloxy group or a 2-naphthyloxy group.

Nonlimiting examples of the arylthio group represented by $R_1$ through $R_{10}$ include phenylthio groups, 1-naphthylthio groups, 2-naphthylthio groups, 4-biphenylthio groups, p-terphenyl-4-ylthio groups, and p-tolylthio groups. For example, the arylthio group may be a phenylthio group or a 2-naphthylthio group.

Nonlimiting examples of the alkoxycarbonyl group represented by $R_1$ through $R_{10}$ include methoxycarbonyl groups, ethoxycarbonyl groups, n-propoxycarbonyl groups, iso-propoxycarbonyl groups, n-butoxycarbonyl groups, and tert-butoxycarbonyl groups. For example, the alkoxycarbonyl group may be a methoxycarbonyl group or an ethoxycarbonyl group.

Nonlimiting examples of the aryl group as a substituent of the amino group, and the aryl group represented by $R_1$ through $R_{10}$, include the same substituents as those listed above with respect to the aryl group represented by $R_1$.

In Formula 1 above, nonlimiting examples of the halogen atom include fluorine atoms, chlorine atoms, bromine atoms, and iodine atoms.

Each of the groups described above may be further substituted, and in some embodiments, may include at least two substituents which may be the same or different. The at least two substituents may be interconnected to form a ring.

Nonlimiting examples of the substituents for Ar and $R_1$ through $R_{10}$ include alkyl groups, alkenyl groups, alkynyl groups, amino groups, alkoxy groups, aryloxy groups, acyl groups, alkoxycarbonyl groups, aryloxycarbonyl groups, acyloxy groups, acylamino groups, alkoxycarbonylamino groups, aryloxycarbonylamino groups, sulfonylamino groups, sulfamoyl groups, carbamoyl groups, alkylthio groups, arylthio groups, sulfonyl groups, sulfinyl groups, ureide groups, phosphoricamide groups, hydroxyl groups, mercapto groups, halogen atoms, cyano groups, sulfo groups, carboxyl groups, nitro groups, hydroxamic acid groups, sulfino groups, hydrazino groups, imino groups, heterocyclic groups, and silyl groups. These substituents may be further substituted. In some embodiments, for example, Ar and $R_1$ through $R_{10}$ may each include at least two substituents which may be the same or different. The at least two substituents may be interconnected to form a ring.

Nonlimiting examples of the alkyl group include C1-C20 alkyl groups. In some embodiments for example, the alkyl group is selected from C1-C12 alkyl groups. In other embodiments, the alkyl group is selected from C1-C8 alkyl groups. Nonlimiting examples of suitable alkyl groups include methyl groups, ethyl groups, iso-propyl groups, tert-butyl groups, n-octyl groups, n-decyl groups, n-hexadecyl groups, cyclopropyl groups, cyclopentyl groups, and cyclohexyl groups.

Nonlimiting examples of the alkenyl group include C2-C20 alkenyl groups. In some embodiments, for example, the alkenyl group is selected from C2-C12 alkenyl groups. In other embodiments, the alkenyl group is selected from C2-C8 alkenyl groups. Nonlimiting examples of the alkenyl group include vinyl groups, allyl groups, 2-butenyl groups, and 3-pentenyl groups.

Nonlimiting examples of the alkynyl group include C2-C20 alkynyl group. In some embodiments, for example, the alkynyl group is a C2-C12 alkynyl group. In other embodiment, the alkynyl group is selected from C2-C8 alkynyl groups. A nonlimiting example of the alkynyl group is a 3-pentynyl group.

Nonlimiting examples of the amino group include C0-C20 amino groups. In some embodiments, for example, the amino group is a C0-C12 amino group. In other embodiments, the amino group is selected from C0-C6 amino groups. Nonlimiting examples of the amino group include amino groups, methylamino groups, dimethylamino groups, diethylamino groups, diphenylamino groups, and dibenzylamino groups.

Nonlimiting examples of the alkoxy group include C1-C20 alkoxy groups. In some embodiments, for example, the alkoxy group is a C1-C12 alkoxy group. In other embodiments, the alkoxy group is selected from C1-C8 alkoxy groups. Nonlimiting examples of the alkoxy group include methoxy groups, ethoxy groups, and butoxy groups.

Nonlimiting examples of the aryloxy group include C6-C20 aryloxy groups. In some embodiments, for example, the aryloxy group is a C6-C16 aryloxy group. In other embodiments, the aryloxy group is selected from C6-C12 aryloxy groups. Nonlimiting examples of the aryloxy group include phenyloxy groups, and 2-naphthyloxy groups.

Nonlimiting examples of the acyl group include C1-C20 acyl groups. In some embodiments, for example, the acyl group is a C1-C16 acyl group. In other embodiments, the acyl group is selected from C1-C12 acyl groups. Nonlimiting examples of the acyl group include acetyl groups, benzoyl groups, formyl groups, and pivaloyl groups.

Nonlimiting examples of the alkoxycarbonyl group include C2-C20 alkoxycarbonyl groups. In some embodiments, for example, the alkoxycarbonyl group is a C2-C16 alkoxycarbonyl group. In other embodiments, the alkoxycarbonyl group is selected from C2-C12 alkoxycarbonyl groups. Nonlimiting examples of the alkoxycarbonyl group include methoxycarbonyl groups, and ethoxycarbonyl groups.

Nonlimiting examples of the aryloxycarbonyl group include C7-C20 aryloxycarbonyl groups. In some embodiments, for example, the aryloxycarbonyl group is a C7-C16 aryloxycarbonyl group. In other embodiments, the aryloxycarbonyl group is selected from C7-C10 aryloxycarbonyl groups. A nonlimiting example of the aryloxycarbonyl group is a phenyloxycarbonyl group.

Nonlimiting examples of the acyloxy group include C2-C20 acyloxy groups. In some embodiments, for example, the acyloxy group is a C2-C16 acyloxy group. In other embodiments, the acyloxy group is selected from C2-C10 acyloxy groups. Nonlimiting examples of the acyloxy group include acetoxy groups and benzoyloxy groups.

Nonlimiting examples of the acylamino group include C2-C20 acylamino groups. In some embodiments, for example, the acylamino group is a C2-C16 acylamino group. In other embodiments, the acylamino group is selected from C2-C10 acylamino groups. Nonlimiting examples of the acylamino group include acetylamino groups, and benzoylamino groups.

Nonlimiting examples of the alkoxycarbonylamino group include C2-C20 alkoxycarbonylamino groups. In some embodiments, for example, the alkoxycarbonylamino group is a C2-C16 alkoxycarbonylamino group. In other embodiments, the alkoxycarbonylamino group is selected from C2-C12 alkoxycarbonylamino groups. A nonlimiting example of a alkoxycarbonylamino group is a methoxycarbonylamino group.

Nonlimiting examples of the aryloxycarbonylamino group include C7-C20 aryloxycarbonylamino groups. In some embodiments, for example, the aryloxycarbonylamino group is a C7-C16 aryloxycarbonylamino group. In other embodiments, the aryloxycarbonylamino group is selected from C7-C12 aryloxycarbonylamino groups. One nonlimiting example of an aryloxycarbonylamino group is a phenyloxycarbonylamino group.

Nonlimiting examples of the sulfonylamino group include C1-C20 sulfonylamino groups. In some embodiments, for example, the sulfonylamino group is a C1-C16 sulfonylamino group. In other embodiments, the sulfonylamino group is selected from C1-C12 sulfonylamino groups. Nonlimiting examples of the sulfonylamino group include methanesulfonylamino groups, and benzenesulfonylamino groups.

Nonlimiting examples of the sulfamoyl group include C0-C20 sulfamoyl groups. In some embodiments, for example, the sulfamoyl group is a C0-C16 sulfamoyl group. In other embodiments, the sulfamoyl group is selected from C0-C12 sulfamoyl groups. Nonlimiting examples of the sulfamoyl group include sulfamoyl groups, methylsulfamoyl groups, dimethylsulfamoyl groups, and phenylsulfamoyl groups.

Nonlimiting examples of the carbamoyl group include C1-C20 carbamoyl groups. In some embodiment, for example, the carbamoyl group is a C1-C16 carbamoyl group. In other embodiments, the carbamoyl group is selected from C1-C12 carbamoyl groups. Nonlimiting examples of the carbamoyl group include carbamoyl groups, methylcarbamoyl groups, diethylcarbamoyl groups, and phenylcarbamoyl groups.

Nonlimiting examples of the alkylthio group include C1-C20 alkylthio groups. In some embodiments, for example, the alkylthio group is a C1-C16 alkylthio group. In other embodiments, the alkylthio group is selected from C1-C12 alkylthio groups. Nonlimiting examples of the alkylthio group include methylthio groups, and ethylthio groups.

Nonlimiting examples of the arylthio group include C6-C20 arylthio groups. In some embodiments, for example, the arylthio group is a C6-C16 arylthio group. In other embodiments, the arylthio group is selected from C6-C12 arylthio groups. One nonlimiting example of the arylthio group is a phenylthio group.

Nonlimiting examples of the sulfonyl group include C1-C20 sulfonyl groups. In some embodiments, for example, the sulfonyl group is a C1-C16 sulfonyl group. In other embodiments, the sulfonyl group is selected from C1-C12 sulfonyl groups. Nonlimiting examples of the sulfonyl group include mesyl groups, and tosyl groups.

Nonlimiting examples of the sulfinyl group include C1-C20 sulfinyl groups. In some embodiments, for example, the sulfinyl group is a C1-C16 sulfinyl group. In other embodiments, the sulfinyl group is selected from C1-C12 sulfinyl groups. Nonlimiting examples of the sulfinyl group include methanesulfinyl groups, and benzenesulfinyl groups.

Nonlimiting examples of the ureide group include C1-C20 ureide groups. In some embodiments, for example, the ureide group is a C1-C16 ureide group. In other embodiments, the ureide group is selected from C1-C12 ureide groups. Nonlimiting examples of the ureide group include ureide groups, methylureide groups, and phenylureide groups.

Nonlimiting examples of the phosphoricamide group include C1-C20 phosphoricamide group. In some embodiments, for example, the phosphoricamide group is a C1-C16 phosphoricamide group. In other embodiments, the phosphoricamide group is selected from C1-C12 phosphoricamide groups. Nonlimiting examples of the phosphoricamide group include diethylphosphoricamide groups, and phenylphosphoricamide groups.

Nonlimiting examples of the halogen atom include fluorine atoms, chlorine atoms, bromine atoms and iodine atoms.

The heterocyclic group may be a C1-C30 heterocyclic group. In some embodiments, for example, the heterocyclic group is a C1-C15 heterocyclic group. Nonlimiting examples of the heterocyclic group include imidazolyl groups, pyridyl groups, quinolyl groups, furyl groups, thienyl groups, piperidyl groups, morpholino groups, benzoxazolyl groups, benzimidazolyl groups, benzothiazolyl groups, and carbazolyl groups, in which the hetero atom may be nitrogen, oxygen, or sulfur.

Nonlimiting examples of the silyl group include C3-C40 silyl groups. In some embodiments, for example, the silyl group is a C3-C30 silyl group. In other embodiments, the silyl group is selected from C3-C24 silyl groups. Nonlimiting examples of the silyl group include trimethylsilyl groups and triphenylsilyl groups.

In some embodiments of the present invention, the heterocyclic compound represented by Formula 1 may include a compound selected from compounds represented by Formulae 2 through 5 below:

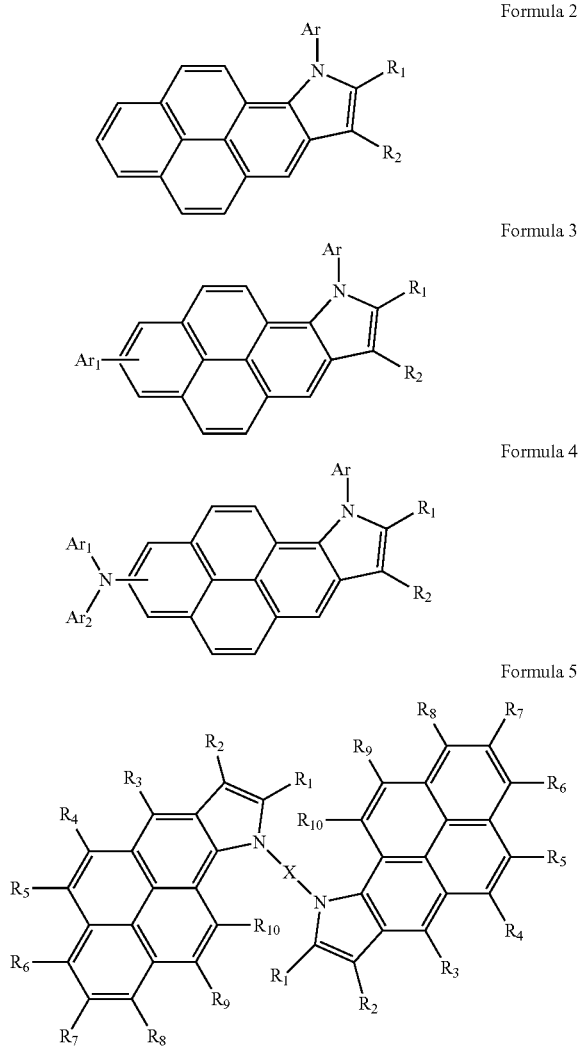

Formula 2

Formula 3

Formula 4

Formula 5

In Formulae 2 through 5, each of Ar, $Ar_1$, and $Ar_2$ may be independently selected from substituted and unsubstituted $C_6$-$C_{60}$ aryl groups, substituted and unsubstituted $C_4$-$C_{60}$ heteroaryl groups, amino groups substituted with at least one substituted or unsubstituted $C_5$-$C_{50}$ aryl group, and substituted and unsubstituted $C_6$-$C_{60}$ condensed polycyclic groups. X may be selected from substituted and unsubstituted $C_6$-$C_{30}$ arylene groups, substituted and unsubstituted $C_4$-$C_{30}$ heteroarylene groups, and substituted and unsubstituted $C_6$-$C_{30}$ condensed polycyclic groups. Each of $R_1$ through $R_{10}$ may be independently selected from hydrogen atoms, heavy hydrogen atoms, substituted and unsubstituted $C_1$-$C_{50}$ alkyl groups, substituted and unsubstituted $C_1$-$C_{50}$ alkoxy groups, substituted and unsubstituted $C_1$-$C_{50}$ alkoxycarbonyl groups, substituted and unsubstituted $C_6$-$C_{60}$ aryl groups, substituted and unsubstituted $C_5$-$C_{50}$ aryloxy groups, substituted and unsubstituted $C_5$-$C_{50}$ arylthio groups, amino groups substituted with at least one substituted or unsubstituted $C_5$-$C_{50}$ aryl group, substituted and unsubstituted $C_3$-$C_{50}$ carbon rings, substituted and unsubstituted $C_4$-$C_{60}$ heteroaryl groups, substituted and unsubstituted $C_4$-$C_{60}$ heterocyclic groups, substituted and unsubstituted $C_6$-$C_{60}$ condensed polycyclic groups, halogen atoms, cyano groups, hydroxyl groups, and carboxyl groups.

According to embodiments of the present invention, in Formulae 2 through 5, each of Ar, $Ar_1$, and $Ar_2$ may be independently selected from monocyclic to tricyclic aryl groups. Nonlimiting examples of suitable monocyclic to tricyclic aryl groups include phenyl groups, naphthyl groups, biphenyl groups, terphenyl groups, fluorenyl groups, and carbazolyl groups. The monocyclic to tricyclic aryl group may be substituted with from one to three substituents. Nonlimiting examples of these substituents include $C_1$-$C_6$ alkyl groups, $C_1$-$C_6$ alkoxy groups, cyano groups, amino groups, phenoxy groups, phenyl groups, and halogen atoms.

In Formulae 2 to 5, each of $R_1$ through $R_{10}$ may be independently selected from hydrogen atoms, heavy hydrogen atoms, methyl groups, substituted and unsubstituted monocyclic to tricyclic aryl groups, and —N(R')(R") groups (in which each of R' and R" may be independently selected from $C_6$-$C_{50}$ aryl groups and $C_3$-$C_{50}$ heteroaryl groups). Nonlimiting examples of the monocyclic to tricyclic aryl group include phenyl groups, naphthyl groups, biphenyl groups, terphenyl groups, fluorenyl groups, and carbazolyl groups. Nonlimiting examples of the substituted monocyclic to tricyclic aryl group include groups with one to three substituents selected from $C_1$-$C_6$ alkyl groups, $C_1$-$C_6$ alkoxy groups, cyano groups, —N(R')(R") groups (in which each of R' and R" may be independently selected from hydrogen atoms, $C_1$-$C_{20}$ alkyl groups, $C_6$-$C_{20}$ aryl groups, and $C_3$-$C_{20}$ heteroaryl groups), $C_1$-$C_5$ alkyl phenoxy groups, phenyl groups, and halogen atoms.

In Formula 5, X may be selected from phenylene groups, biphenylene groups, terphenylene groups, quaterphenylene groups, naphthylene groups, anthracenylene groups, phenanthrylene groups, chrysenylene groups, pyrenylene groups, perylenylene groups, fluorenylene groups, thiophenylene groups, 1-phenylthiophenylene groups, 1,4-diphenylthiophenylene groups, benzothiophenylene groups, 1-phenylbenzothiophenylene groups, 1,8-diphenylbenzothiophenylene groups, furylene groups, 1-phenyldibenzothiophenylene groups, 1,8-diphenylthiophenylene groups, dibenzofuranylene groups, 1-phenyldibenzofuranylene groups, 1,8-diphenyldibenzofuranylene groups, and benzothiazolylene groups. Nonlimiting examples of the heteroarylene group represented by X include thiophenylene groups, 1-phenylthiophenylene groups, 1,4-diphenylthiophenylene groups, benzothiophenylene groups, 1-phenylbenzothiophenylene groups, 1,8-diphenylbenzothiophenylene groups, furylene groups, 1-phenyldibenzothiophenylene groups, 1,8-diphenylthiophenylene groups, dibenzofuranylene groups, 1-phenyldibenzofuranylene groups, 1,8-diphenyldibenzofuranylene groups, and benzothiazolylene groups. For example, in some embodiments, the heteroarylene group may be a 1-phenylthiophenyl group, a 1-phenylbenzothiophenyl group, a 1-phenyldibenzofuranyl group, or a benzothiazolyl group.

In Formula 1, and Formulae 2 to 5, each of Ar, Ar$_1$, and Ar$_2$ may be selected from the below groups, but are not limited thereto.
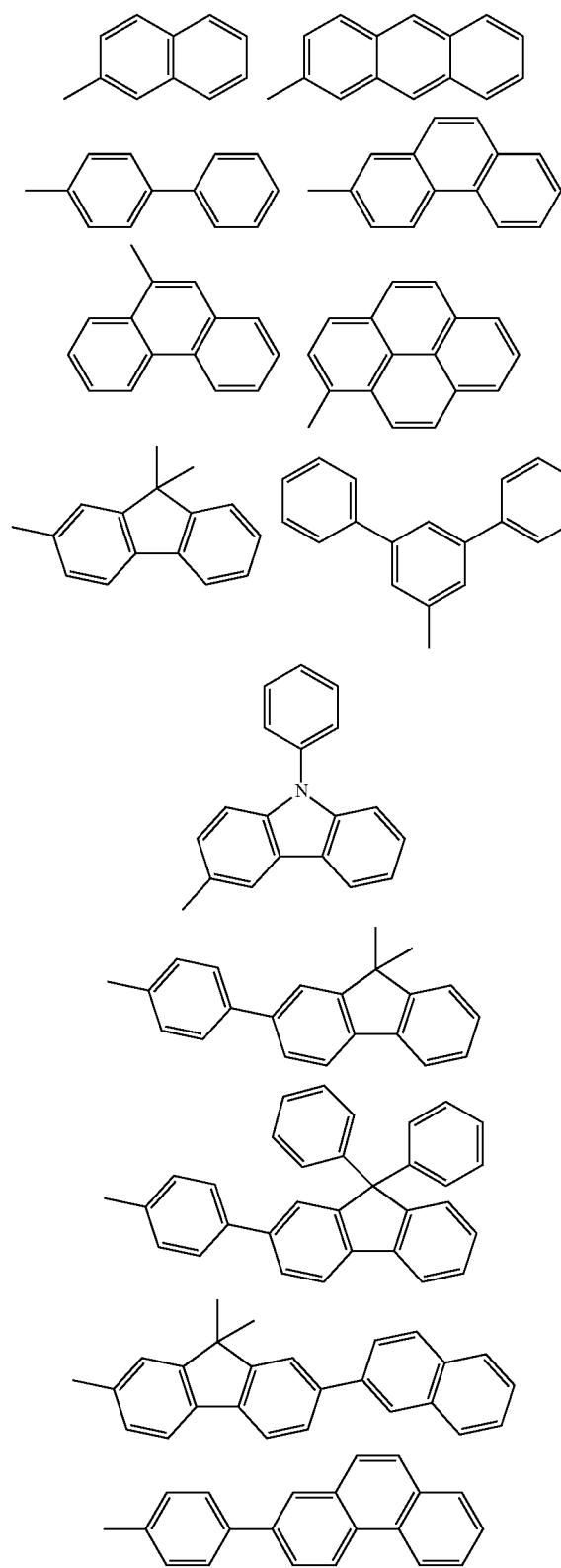
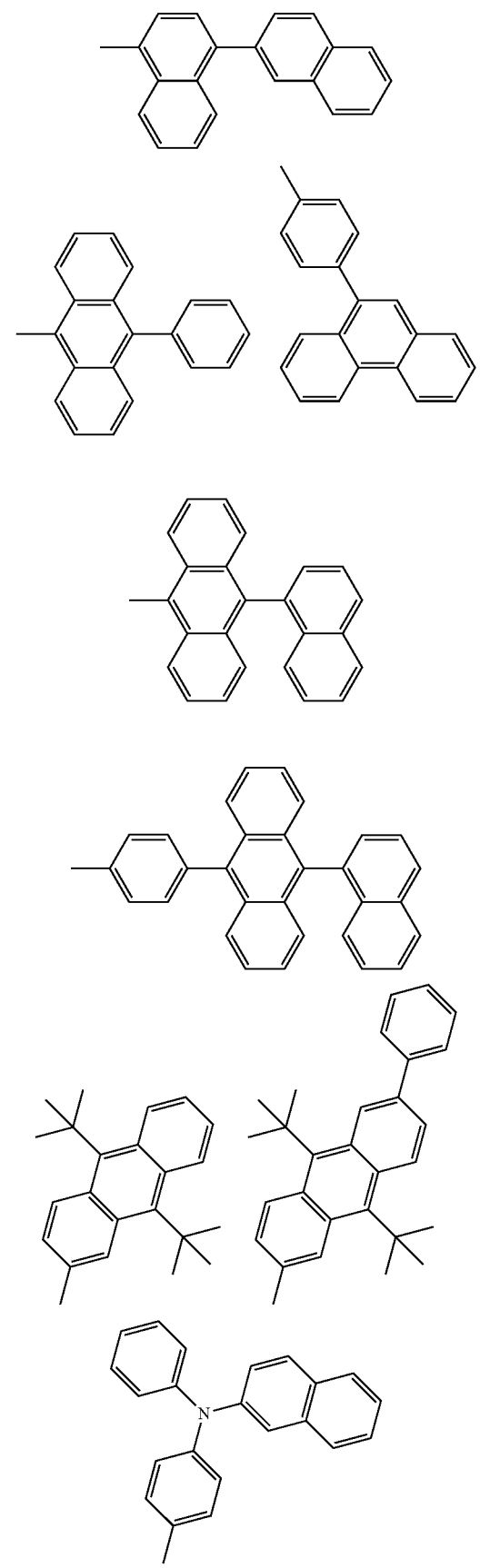

-continued

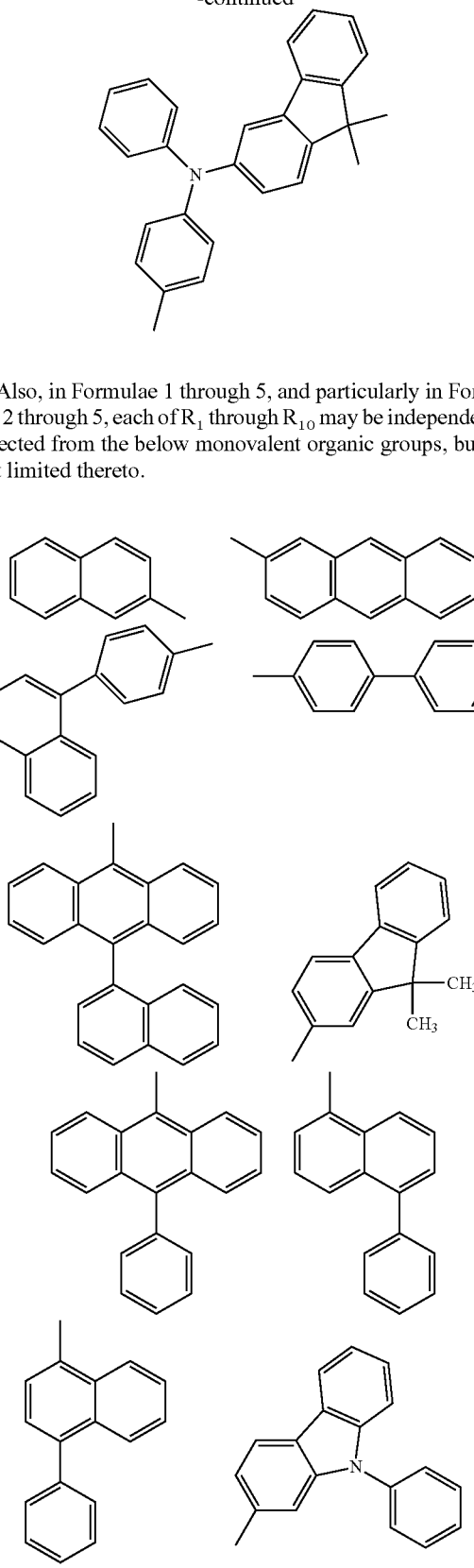

Also, in Formulae 1 through 5, and particularly in Formulae 2 through 5, each of $R_1$ through $R_{10}$ may be independently selected from the below monovalent organic groups, but are not limited thereto.

In Formula 5 above, X may be selected from the following groups, but is not limited thereto.

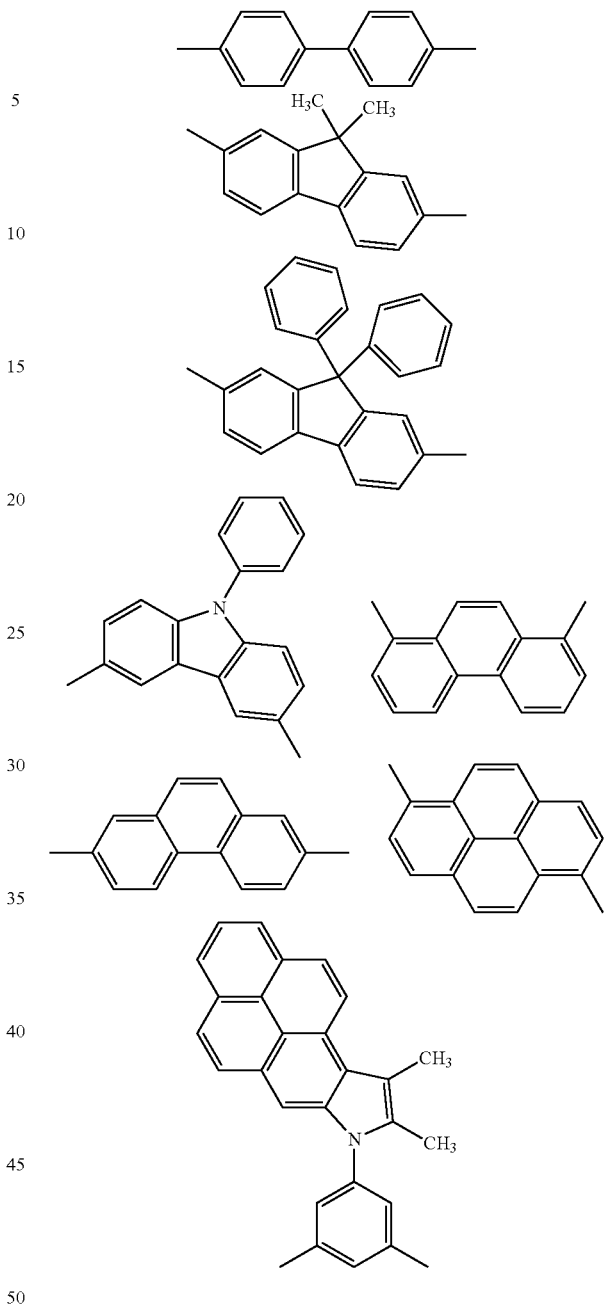

Hereinafter, substituents described with reference to Formulae 1 through 6 will be described.

The unsubstituted $C_1$-$C_{50}$ alkyl group may be linear or branched. Nonlimiting examples of the alkyl group include methyl groups, ethyl groups, propyl groups, isobutyl groups, sec-butyl groups, pentyl groups, iso-amyl groups, hexyl groups, heptyl groups, octyl groups, nonanyl groups, and dodecyl groups. At least one hydrogen atom of the alkyl group may be substituted with a substituent selected from heavy hydrogen atoms, halogen atoms, hydroxyl groups, nitro groups, cyano groups, amino groups, amidino groups, hydrazines, hydrazones, carboxyl groups and salts thereof, sulfonic acid groups and salts thereof, phosphoric acid groups and salts thereof, $C_1$-$C_{10}$ alkyl groups, $C_1$-$C_{10}$ alkoxy groups, $C_2$-$C_{10}$ alkenyl groups, $C_2$-$C_{10}$ alkynyl groups, $C_6$-$C_{16}$ aryl groups, and $C_4$-$C_{16}$ heteroaryl groups.

The unsubstituted $C_3$-$C_{50}$ carbon ring refers to a $C_3$-$C_{50}$ cycloalkyl group where at least one hydrogen atom in the carbon ring may be substituted with the substituents described above in connection with the $C_1$-$C_{50}$ alkyl group.

The unsubstituted $C_4$-$C_{60}$ heterocyclic group refers to a $C_4$-$C_{60}$ cycloalkyl group including one, two or three hetero atoms selected from N, O, P and S, where at least one hydrogen atom in the heterocyclic group may be substituted with the substituents described above in connection with the $C_1$-$C_{50}$ alkyl group.

The unsubstituted $C_1$-$C_{50}$ alkoxy group is a group having a —OA structure where A is an unsubstituted $C_1$-$C_{50}$ alkyl group as described above. Nonlimiting examples of the alkoxy group include methoxy groups, ethoxy groups, propoxy groups, isopropyloxy groups, butoxy groups, and pentoxy groups. At least one hydrogen atom of the alkoxy group may be substituted with the substituents described above in connection with the $C_1$-$C_{50}$ alkyl group.

The unsubstituted $C_6$-$C_{60}$ aryl group refers to a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with the substituents described above in connection with the $C_1$-$C_{50}$ alkyl group.

Nonlimiting examples of the substituted or unsubstituted $C_6$-$C_{60}$ aryl group include phenyl groups, $C_1$-$C_{10}$ alkylphenyl groups (for example, ethylphenyl groups), halophenyl groups (for example, o-, m-, and p-fluorophenyl groups, dichlorophenyl groups), cyanophenyl groups, dicyanophenyl groups, trifluoromethoxyphenyl groups, biphenyl groups, halobiphenyl groups, cyanobiphenyl groups, $C_1$-$C_{10}$ alkyl biphenyl groups, $C_1$-$C_{10}$ alkoxybiphenyl groups, o-, m-, and p-tolyl groups, o-, m-, and p-cumenyl groups, mesityl groups, phenoxyphenyl groups, (α,α-dimethylbenzene)phenyl groups, (N,N'-dimethyl)aminophenyl groups, (N,N'-diphenyl)aminophenyl groups, pentalenyl groups, indenyl groups, naphthyl groups, halonaphthyl groups (for example, fluoronaphthyl groups), $C_1$-$C_{10}$ alkylnaphthyl groups (for example, methylnaphthyl groups), $C_1$-$C_{10}$ alkoxynaphthyl groups (for example, methoxynaphthyl groups), cyanonaphthyl groups, anthracenyl groups, azulenyl groups, heptalenyl groups, acenaphthylenyl groups, phenalenyl groups, fluorenyl groups, anthraquinolyl groups, methylanthryl groups, phenanthryl groups, triphenylene groups, pyrenyl groups, chrysenyl groups, ethyl-chrysenyl groups, picenyl groups, perylenyl groups, chloroperylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, and ovalenyl groups.

The unsubstituted $C_4$-$C_{60}$ heteroaryl group includes one, two or three hetero atoms selected from N, O, P and S. At least two rings may be fused to each other or linked to each other by a single bond. Nonlimiting examples of the unsubstituted $C_4$-$C_{60}$ heteroaryl group include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, and isoquinolinyl groups. At least one hydrogen atom in the heteroaryl group may be substituted with the substituents described above in connection with the $C_1$-$C_{50}$ alkyl group.

The unsubstituted $C_6$-$C_{60}$ condensed polycyclic group refers to a substituent including at least two rings where at least one aromatic ring and/or at least one non-aromatic ring are fused to each other. The unsubstituted $C_6$-$C_{60}$ polycyclic condensed group may include some of the substituents described in connection with the aryl group or the heteroaryl group.

The heterocyclic compound of Formula 1 may be used as an organic layer material having at least one of electron-injecting capability, electron-transporting capability, and light-emitting capability.

The heterocyclic compound of Formula 1 has a high glass transition temperature (Tg) or melting point due to the introduction of the heterocyclic group. Thus, the heterocyclic compound has high heat resistance against Joule's heat generated in an organic layer, between organic layers, or between an organic layer and a metallic electrode when light emission occurs. The heterocyclic compound also has high durability in a high-temperature environment. An organic light-emitting device manufactured using the heterocyclic compound has high durability when stored or operated.

Nonlimiting examples of the heterocyclic compound of Formula 1 include the following Compounds 1-80:

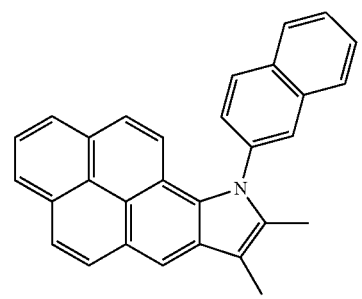

1

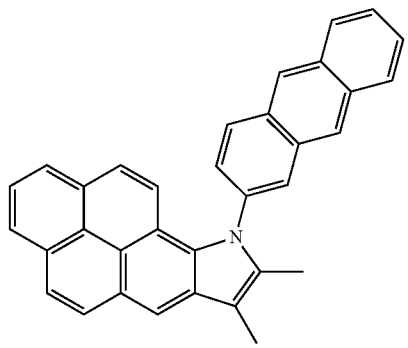

2

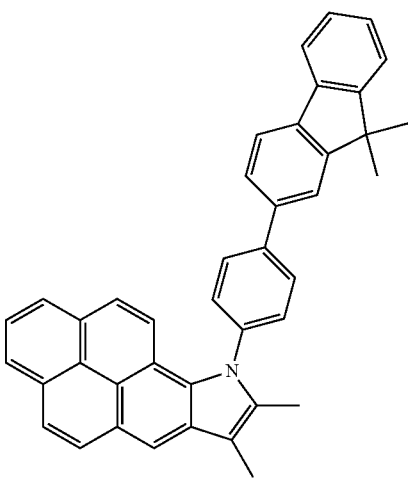

3

4
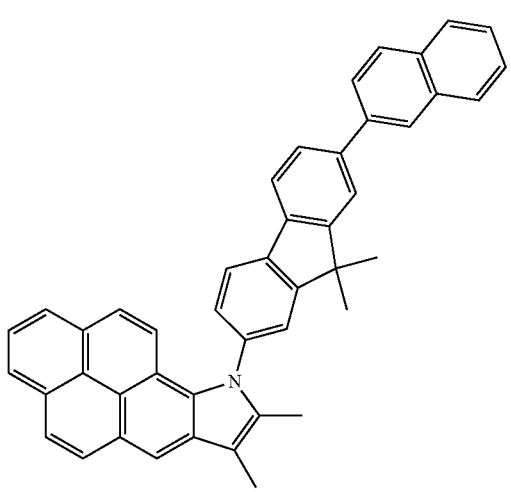
5
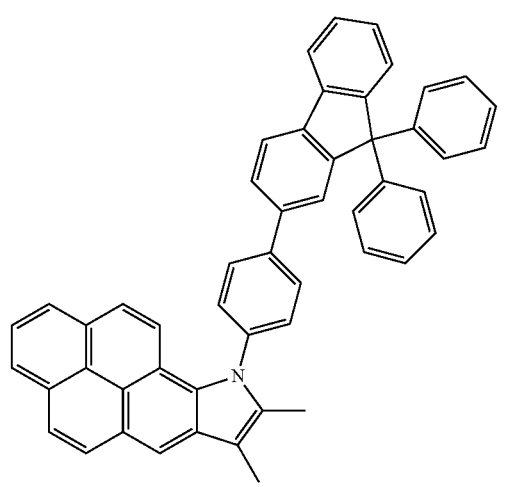
6
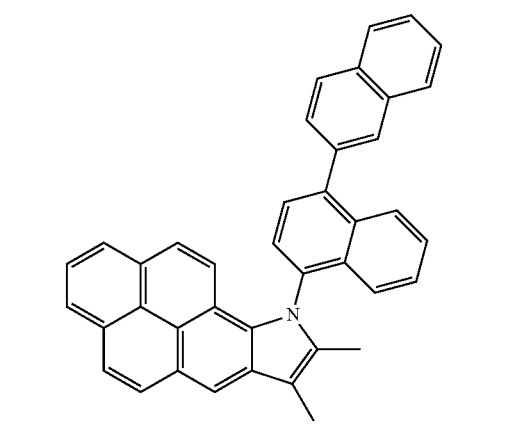
7
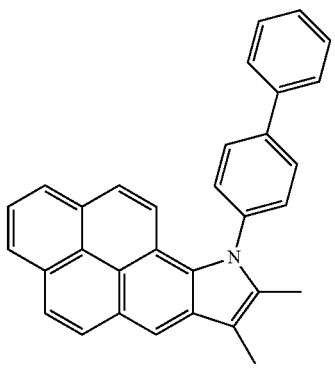
8
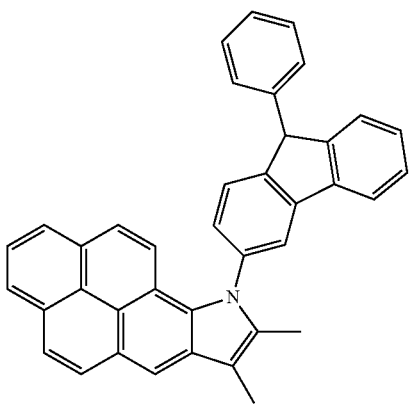
9
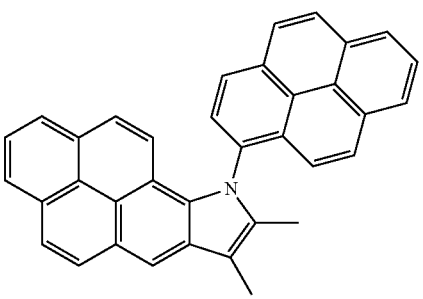
10
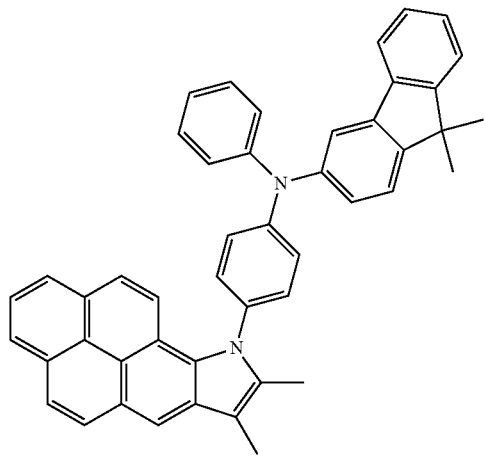

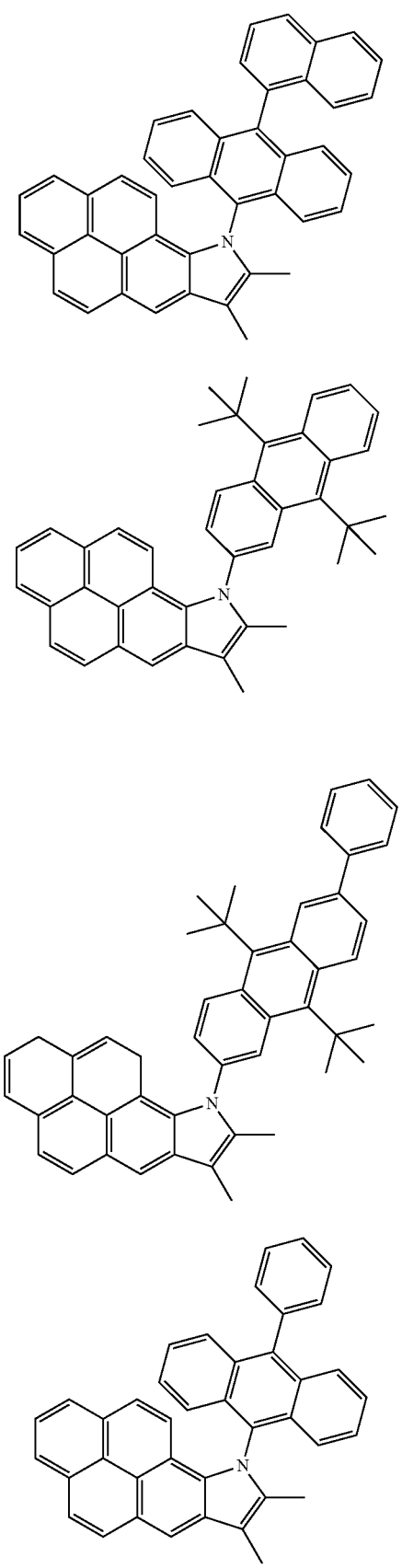
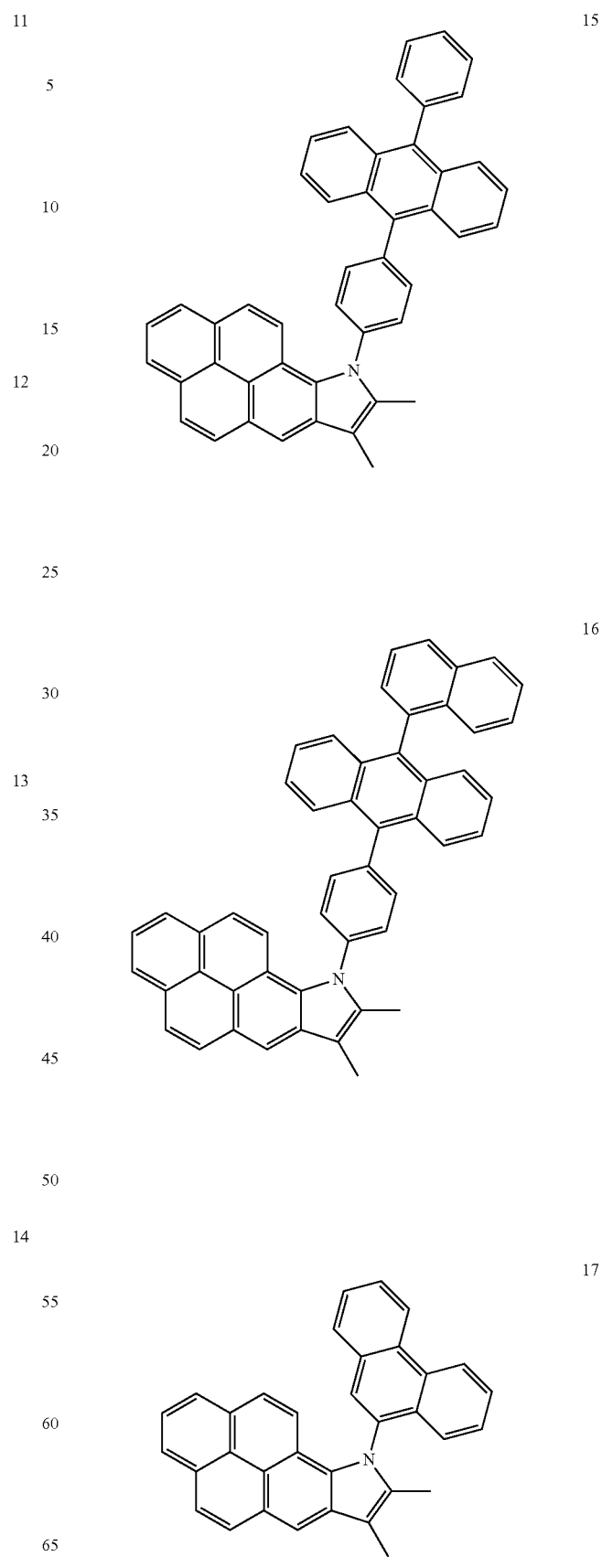

18
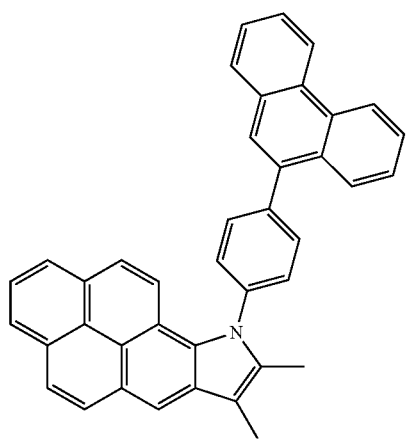
19
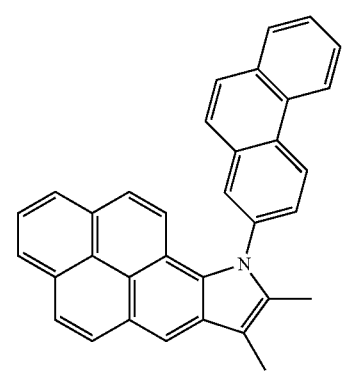
20
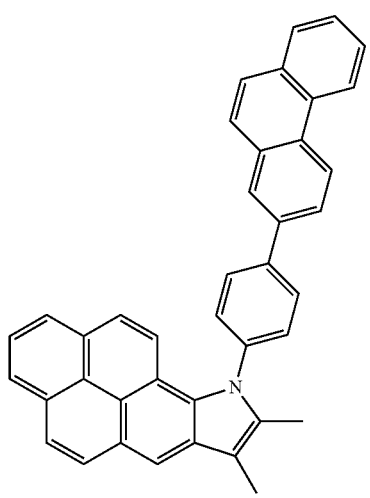
21
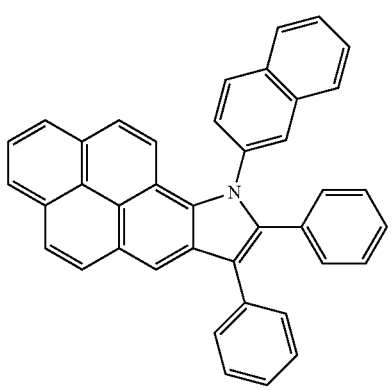
22
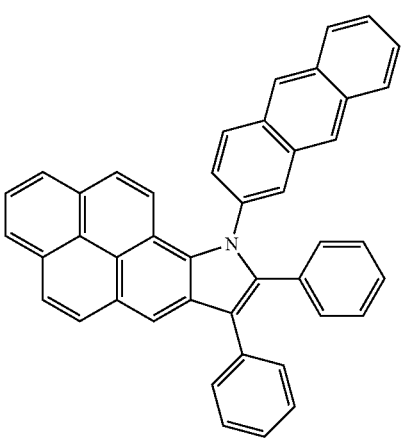
23
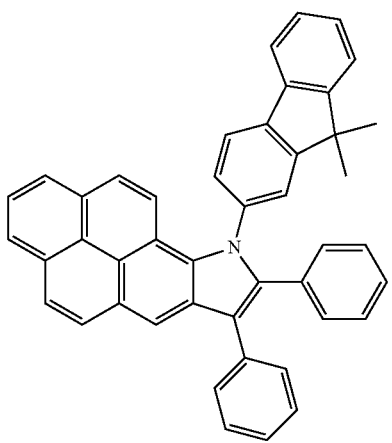

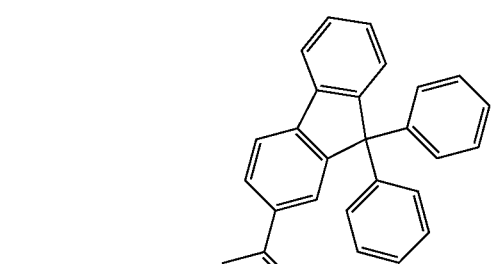
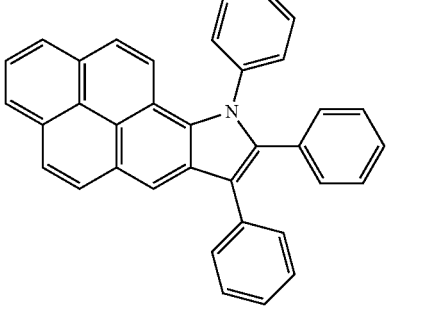
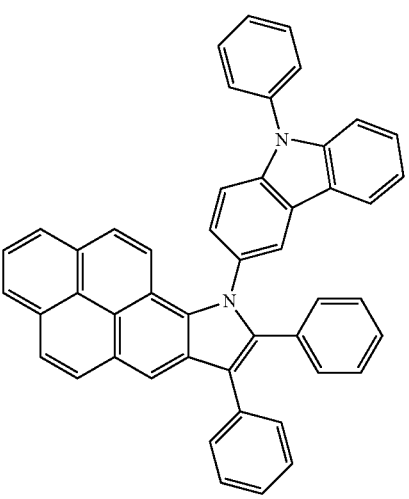
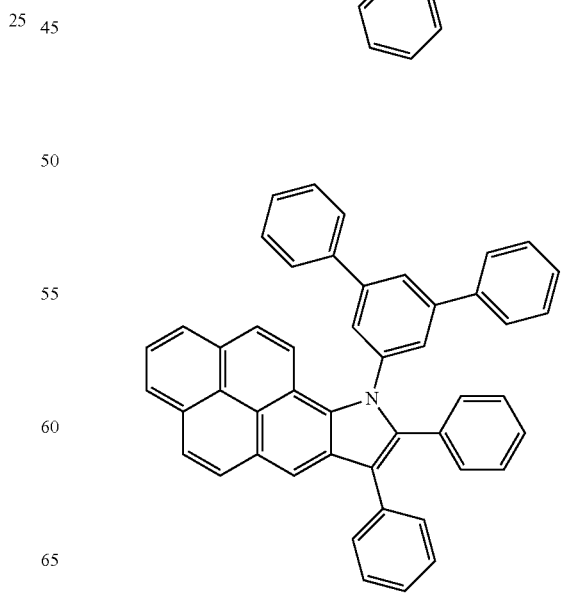

29
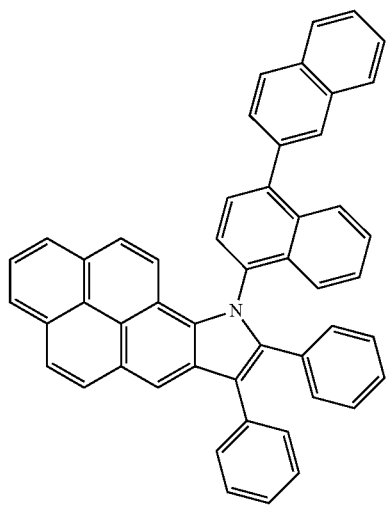
30
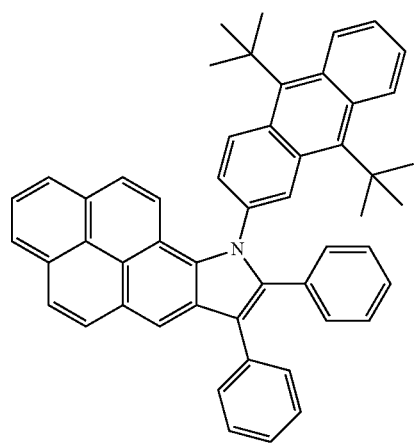
31
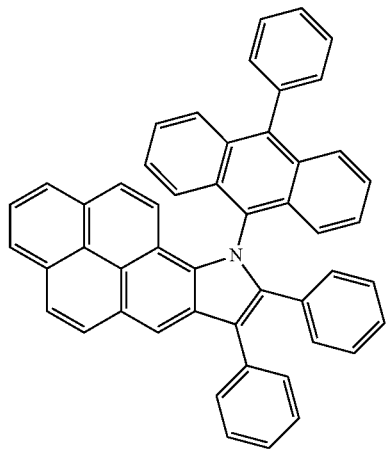
32
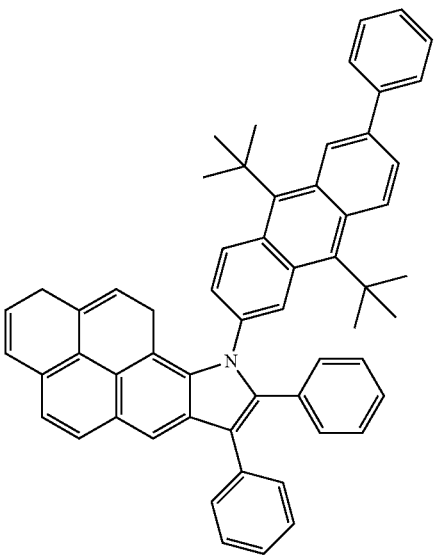
33
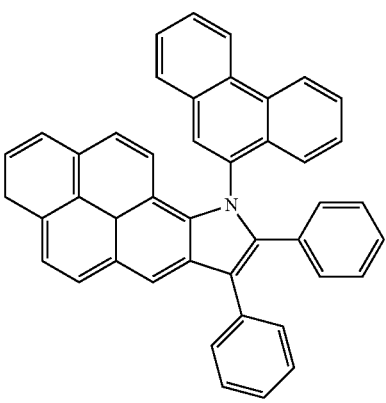
34
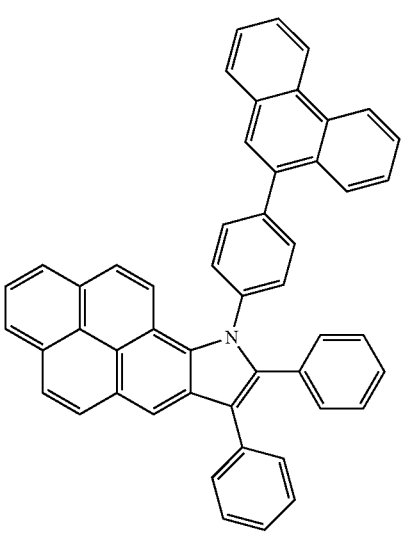

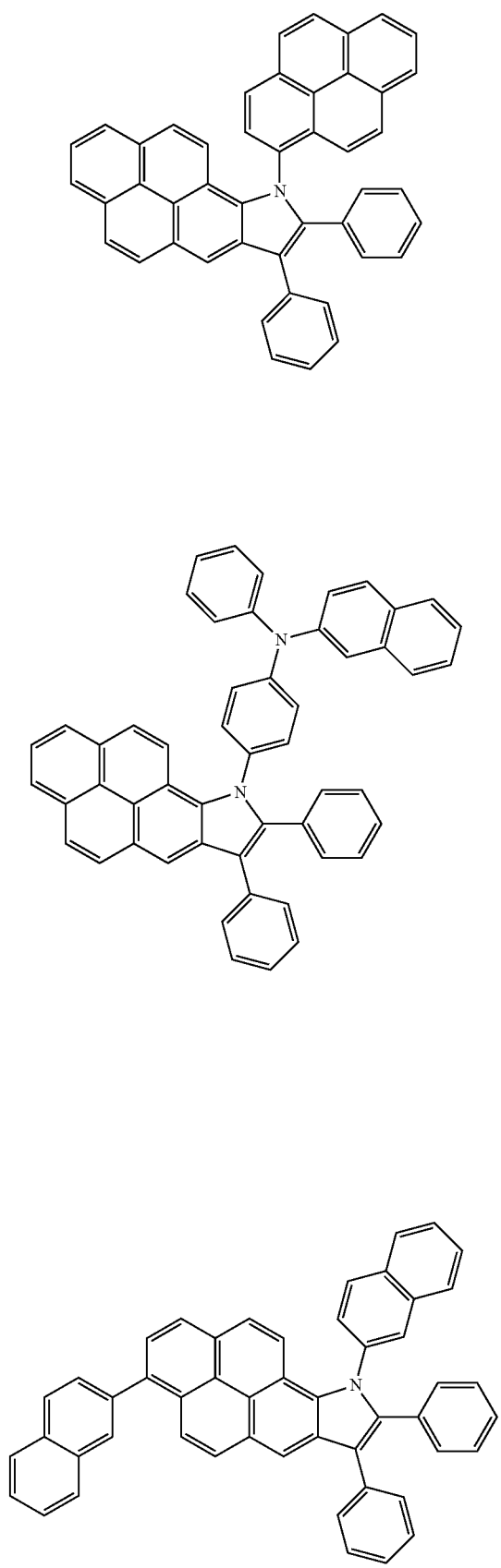
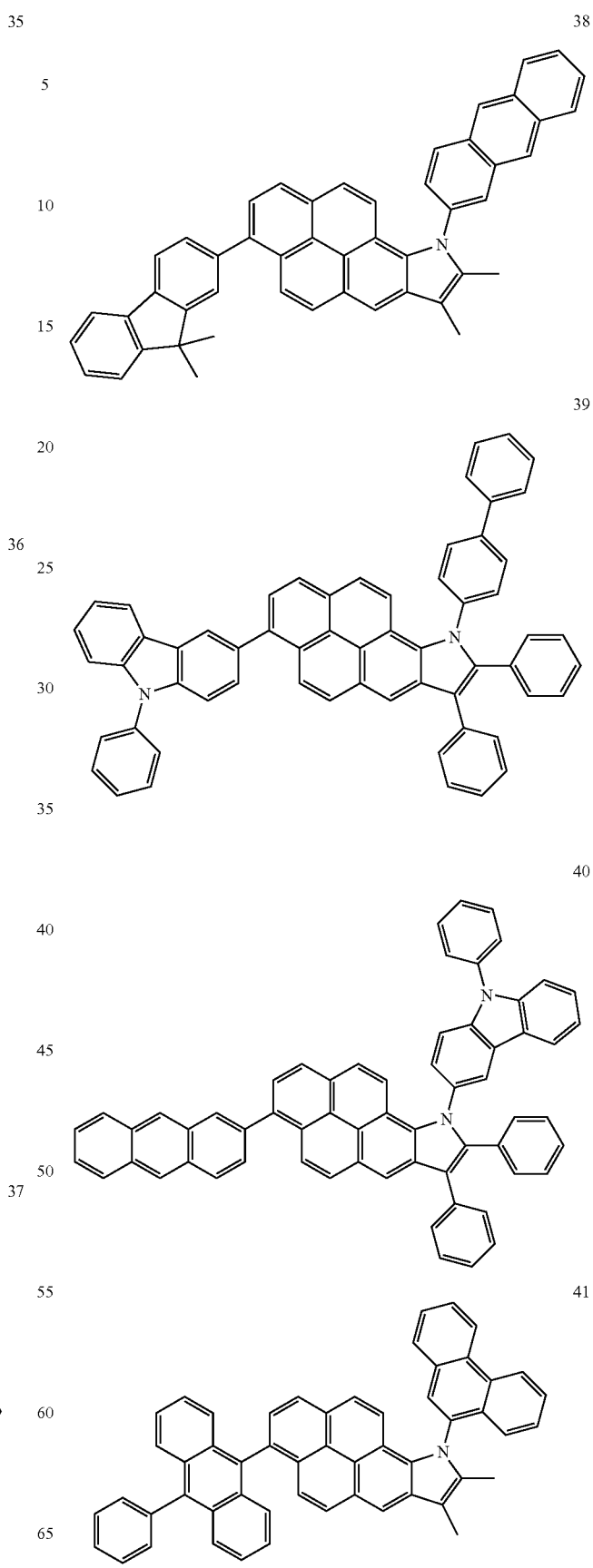

42
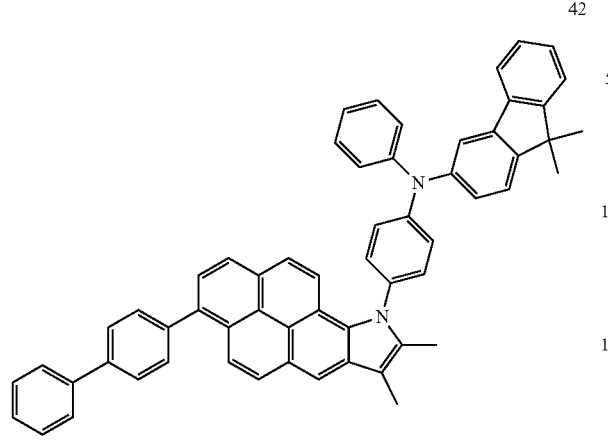
43
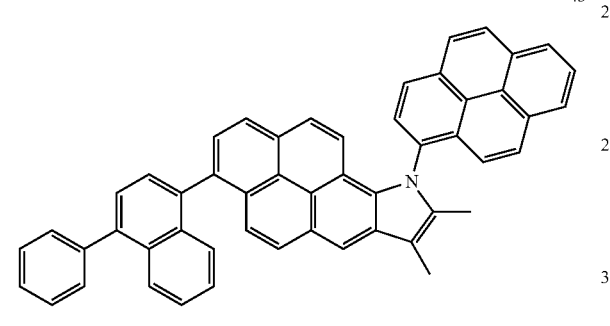
44
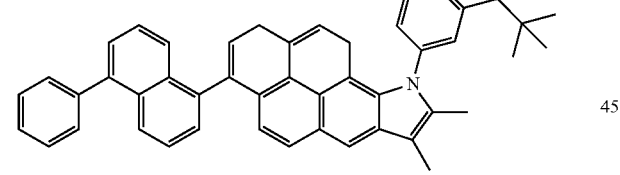
45
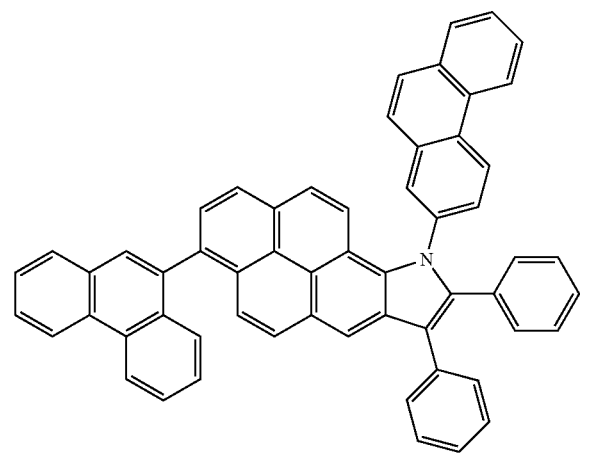
46
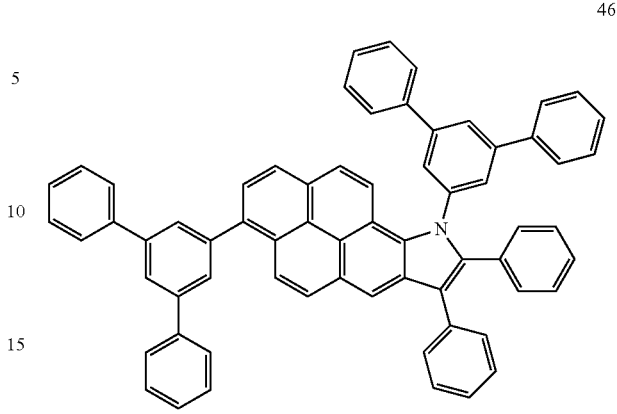
47
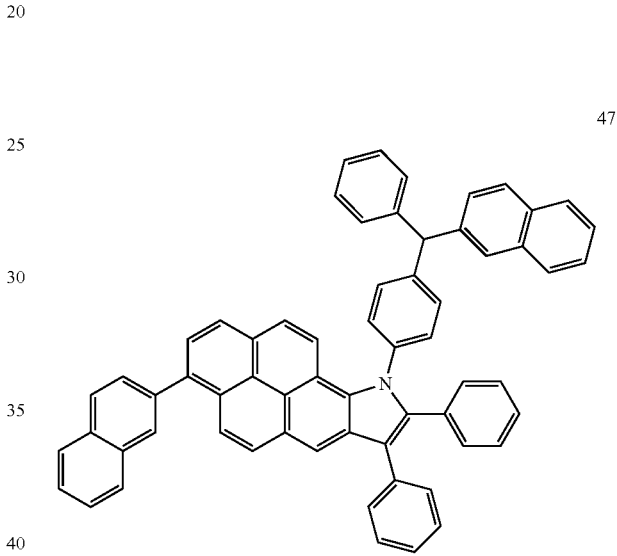
48
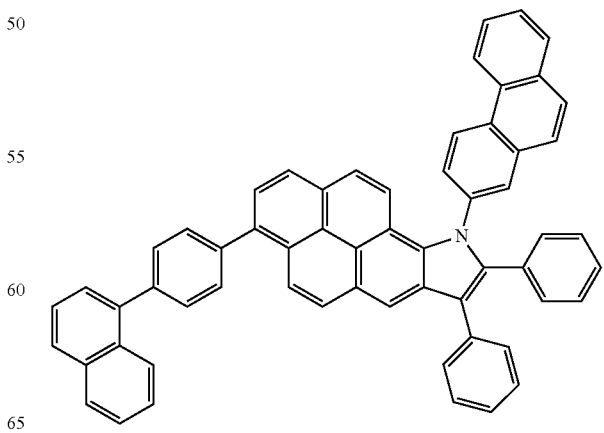

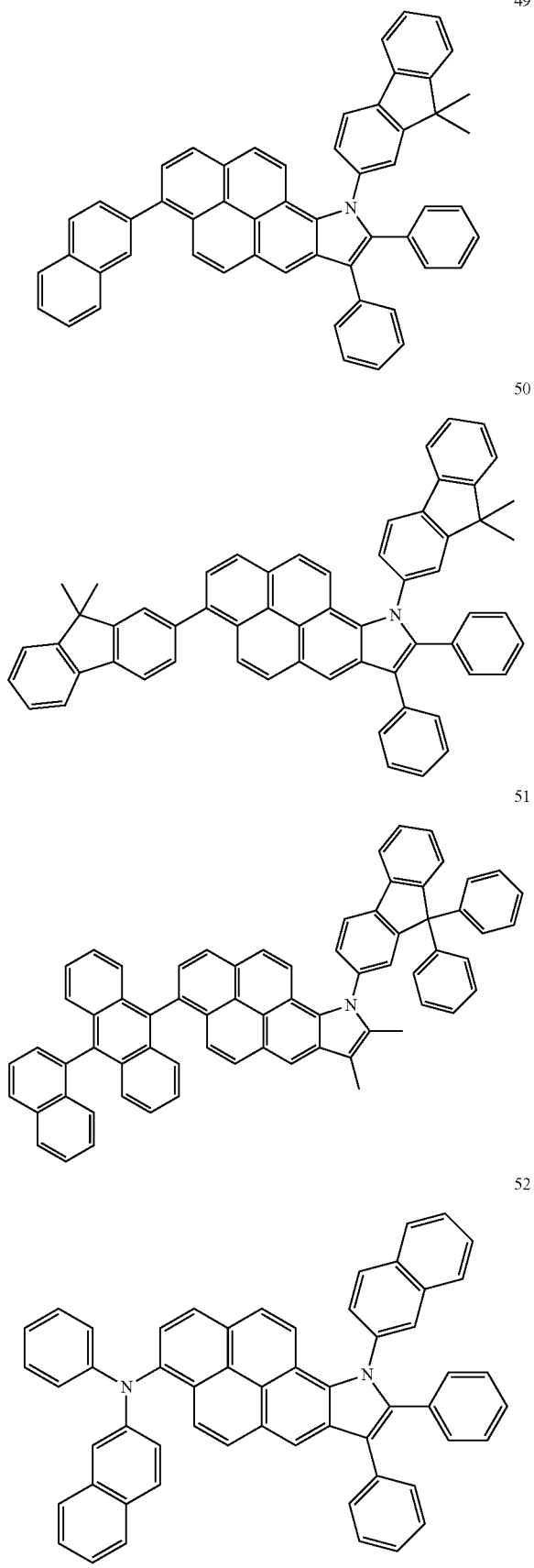
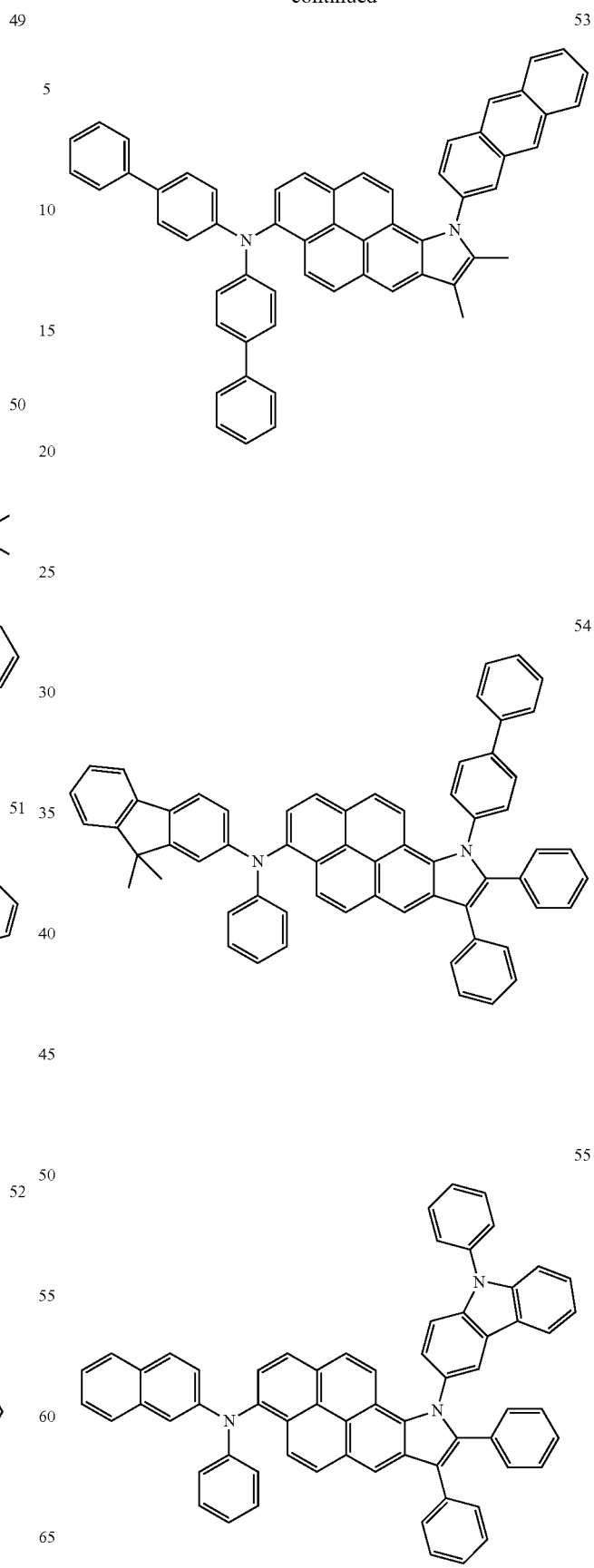

56
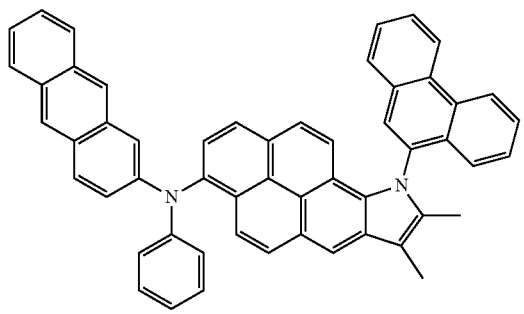
57
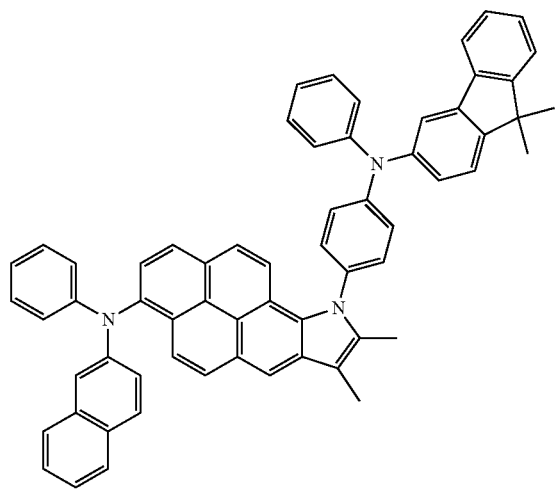
58
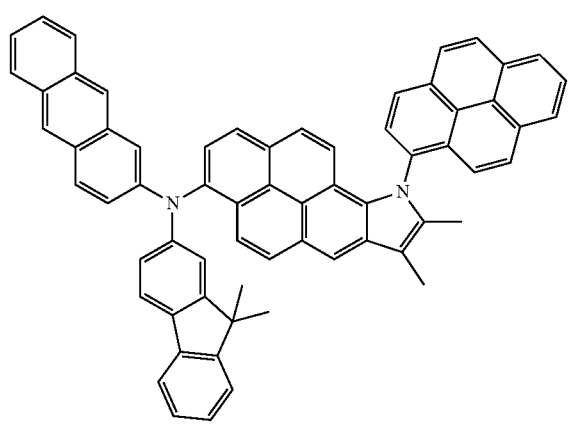
59
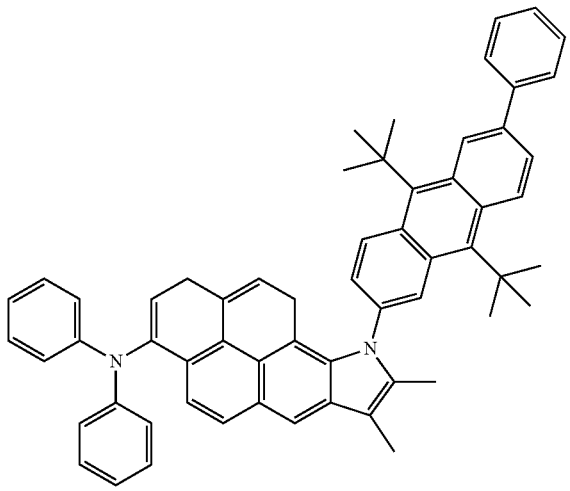
60
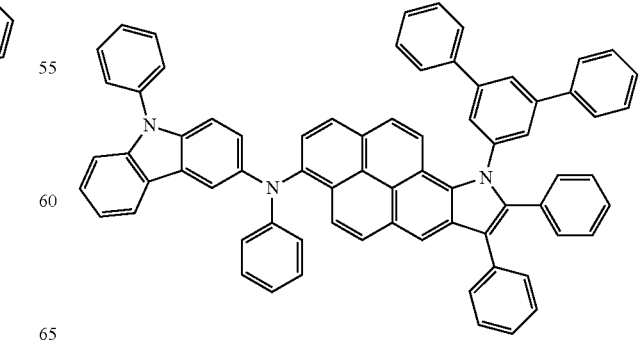
61

62
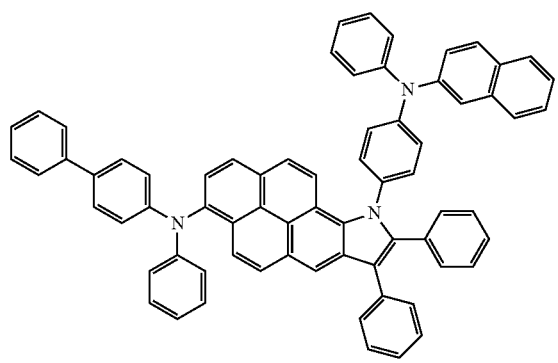
63
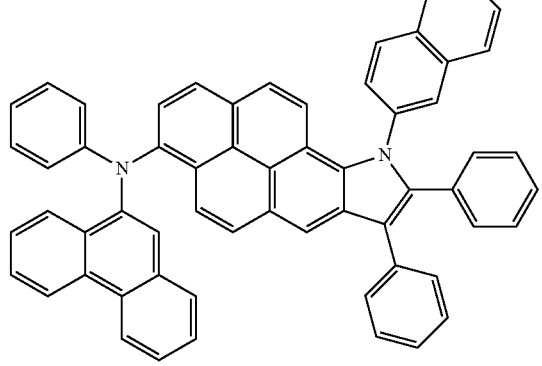
64
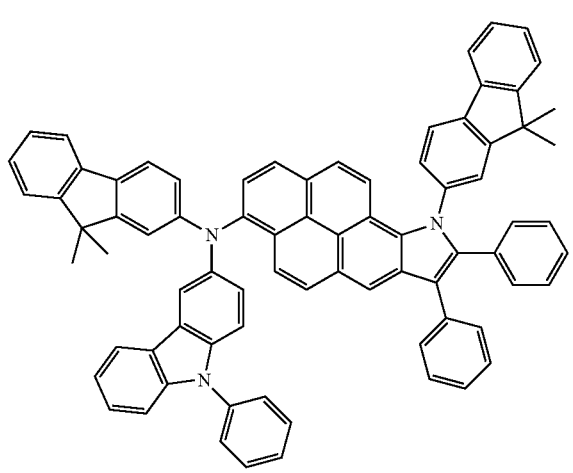
65
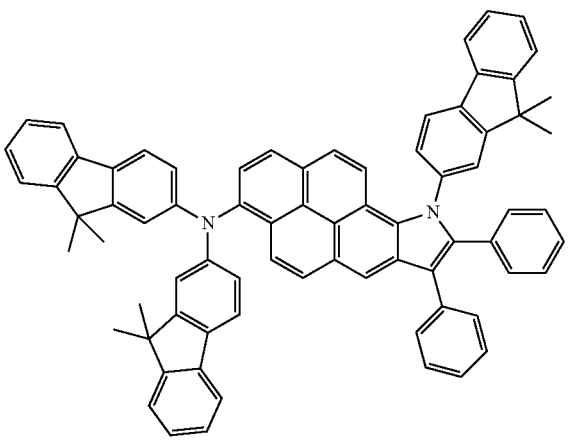
66
67
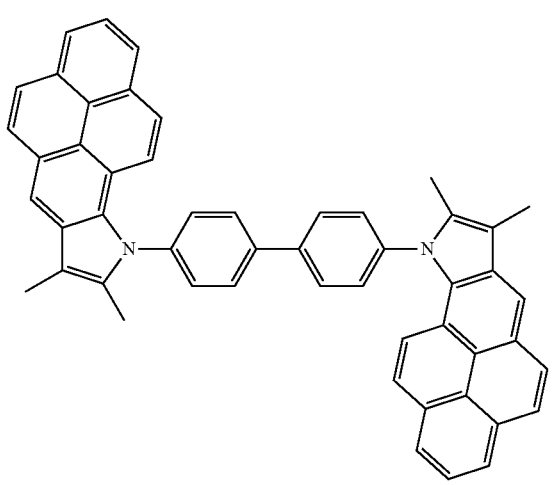

68
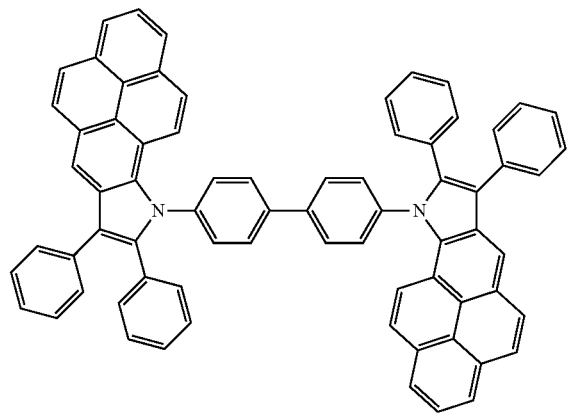
69
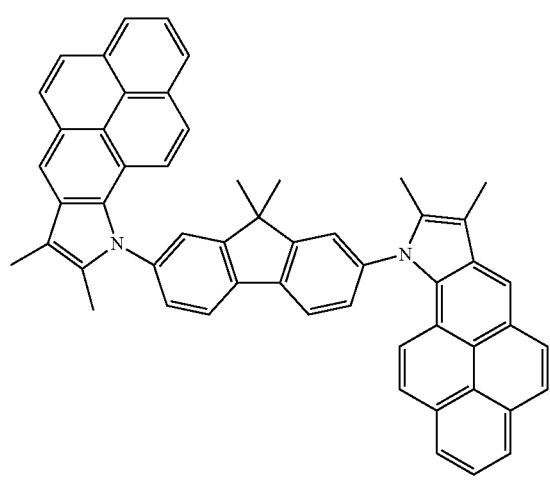
70
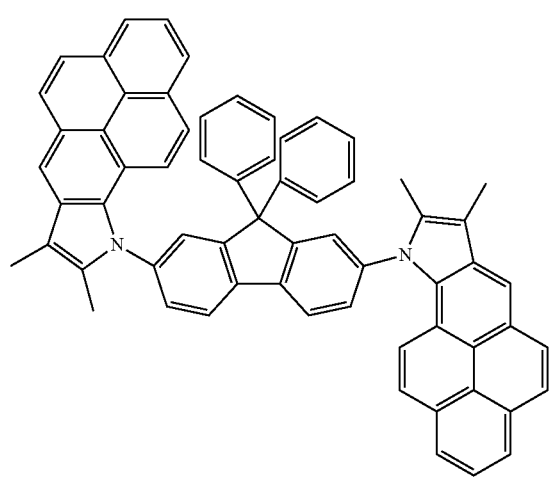
71
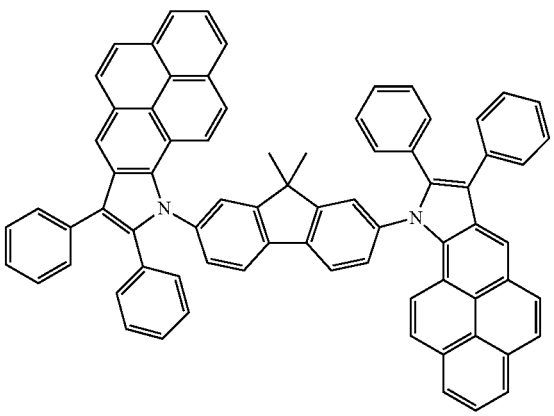
72
73
74
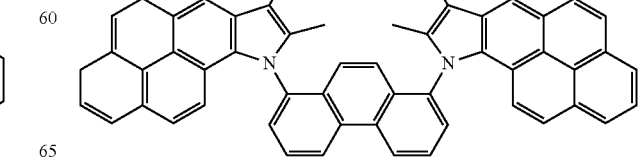

75
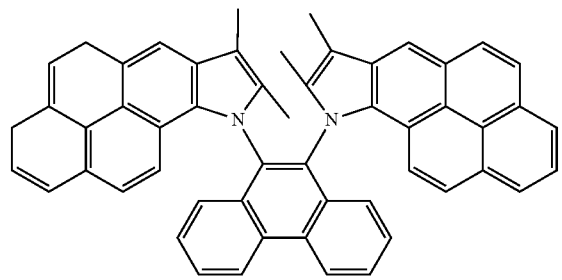
76
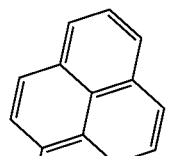
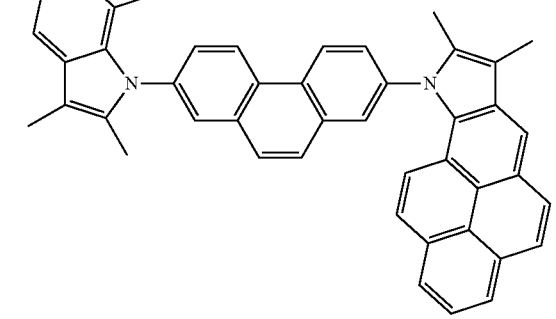
77
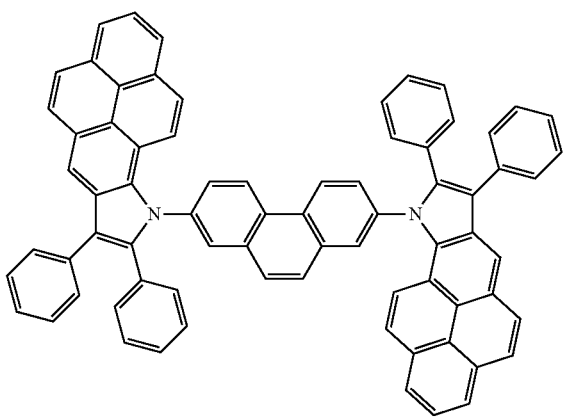
78
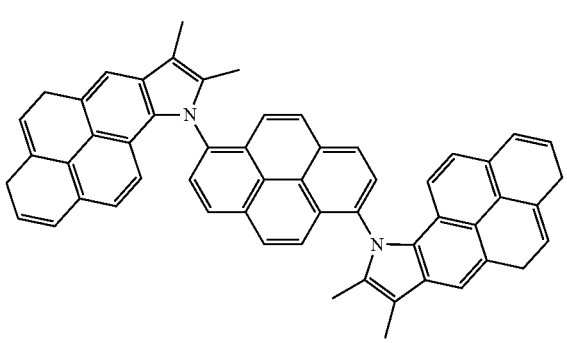
79
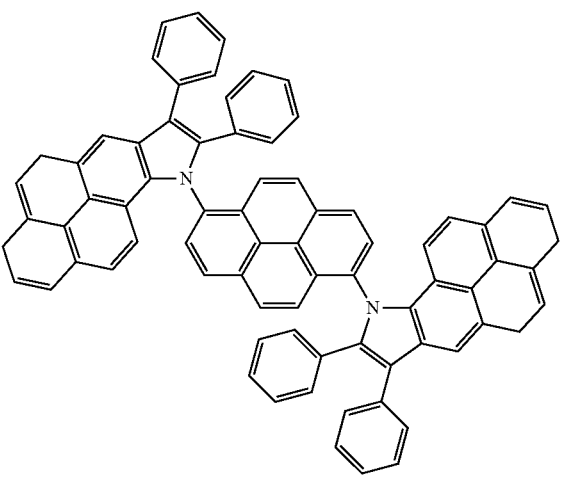
80
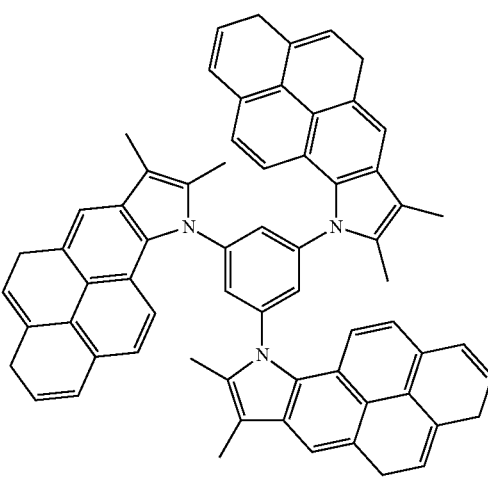
In some embodiments, for example, the heterocyclic compound of Formula 1 is selected from Compound 12, Compound 23, Compound 36, Compound 39, Compound 49, Compound 65 and Compound 67.

39    40
12
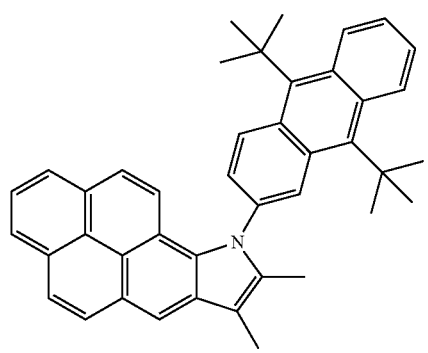
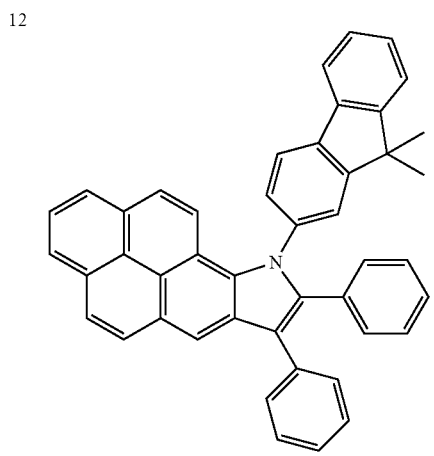
36    39
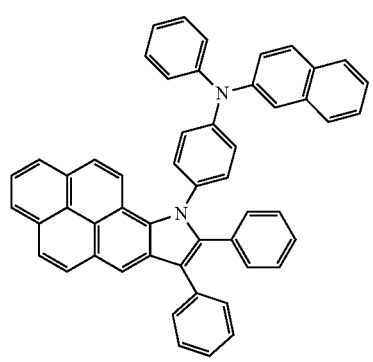
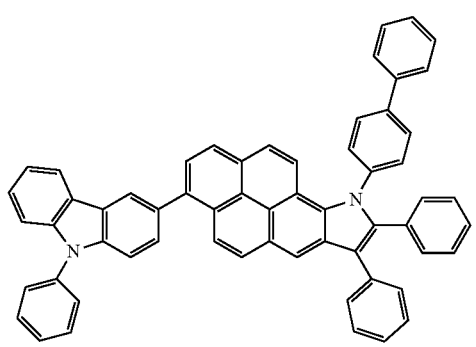
23
49
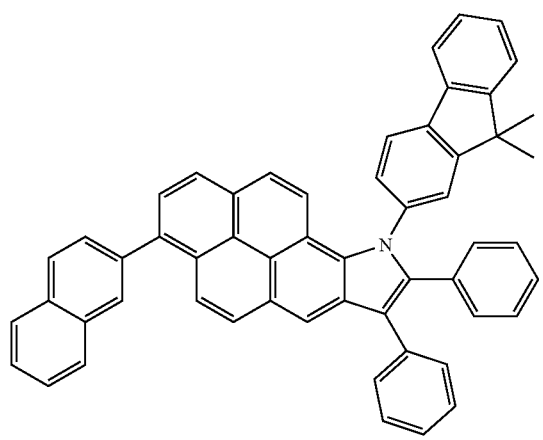

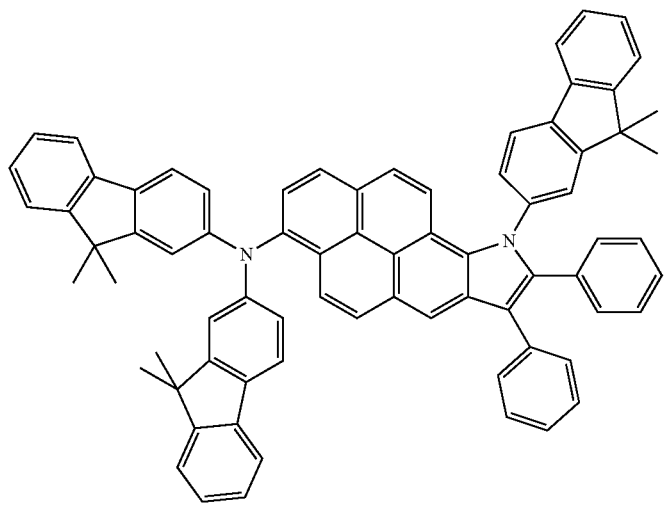

65

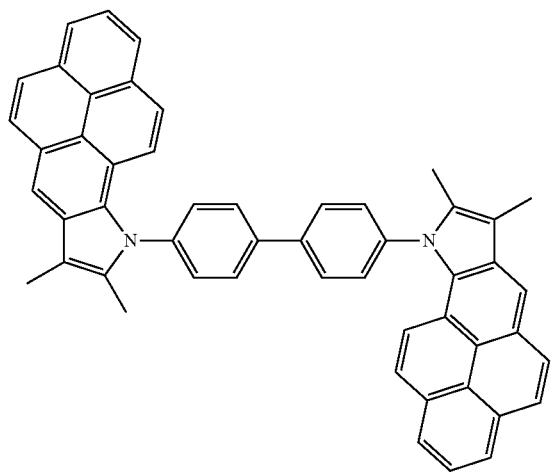

67

According to other embodiments of the present invention, a method of synthesizing a heterocyclic compound of Formula 1 is provided. First, a heterocyclic compound of Formula 8 is prepared according to the following reaction scheme.

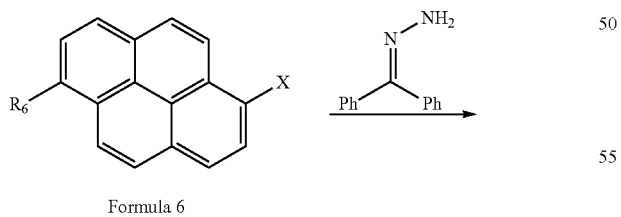

Formula 6

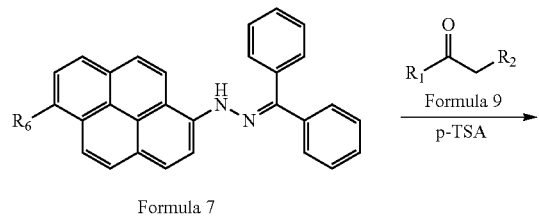

Formula 7

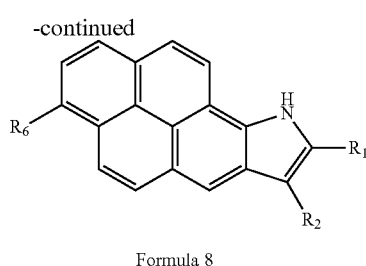

Formula 8

In the above reaction scheme, X is a halogen atom, and $R_1$, $R_2$, and $R_6$ are as defined above with respect to Formula 1.

As illustrated in the reaction scheme above, benzophenone hydrazone, sodium butoxide, palladium diacetate, and 2-dicyclohexylphospino-2',4',6'-triisopropylbiphenyl are added to a heterocyclic compound represented by Formula 6. The components are mixed together and heated to obtain a compound represented by Formula 7.

In the synthesis method, the amount of benzophenone hydrazone may be about 1.05 to about 1.2 moles based on 1 mole of the heterocyclic compound of Formula 6. The amount of sodium butoxide may be about 1.2 to about 1.5 moles based on 1 mole of the heterocyclic compound of Formula 6. In addition, the amount of palladium diacetate may be about 0.02 to about 0.05 moles, and the amount of 2-dicyclohexylphospino-2',4',6'-triisopropylbiphenyl may be about 0.02 to about 0.05 moles, based on 1 mole of the heterocyclic compound of Formula 6.

The heating may be performed at a temperature of about 80 to about 100° C. When the heating temperature is outside this range, a low yield of the compound of Formula 7 may be obtained.

Then, the compound of Formula 7 is mixed with p-toluenesulfonic acid monohydrate and a compound represented by Formula 9, and the mixture is heated to obtain a compound represented by Formula 8.

When the reaction is completed, the reaction product is worked up to obtain the heterocyclic compound of Formula 8, which is a heterocyclic compound represented by Formula 1.

The heating temperature may be about 60° C. to about 100° C. When the heating temperature falls outside this range, a low yield of the compound of Formula 8 may be obtained.

The amount of p-toluenesulfonic acid monohydrate may be about 1.5 to about 2.0 moles, and the amount of the compound of Formula 9 may be about 1.5 to about 2.0 moles, based on 1 mole of the compound of Formula 7. A nonlimiting example of the compound of Formula 9 is benzylphenylketone.

According to other embodiments of the present invention, an organic light-emitting device includes a first electrode, a second electrode, and an organic layer between the first electrode and the second electrode. The organic layer includes at least one organic layer containing the heterocyclic compound of Formula 1 described above. The heterocyclic compound may be used exclusively or may be included in a mixture.

The at least one organic layer containing the heterocyclic compound of Formula 1 may include an electron injection layer, an electron transport layer, or a single layer having both electron injection and electron transport capabilities. The at least one organic layer containing the heterocyclic compound of Formula 1 may include an emission layer. The heterocyclic compound of Formula 1 may be used as a host material for a blue, green, or red fluorescent or phosphorescent material.

In some embodiments, for example, the at least one organic layer containing the heterocyclic compound represented by Formula 1 may include an electron injection layer or an electron transport layer.

The organic layer may include an emission layer, an electron transport layer, and an electron injection layer, where the electron injection layer or the electron transport layer may contain the heterocyclic compound of Formula 1, and the emission layer may contain an anthracene compound.

Alternatively, the organic layer may include an emission layer, an electron transport layer, and an electron injection layer, where the electron injection layer or the electron transport layer may contain the heterocyclic compound of Formula 1, and the emission layer may contain a $C_4$-$C_{50}$ heteroaryl compound or a styryl compound.

The first electrode may be an anode, and the second electrode may be a cathode, but the reverse is also possible.

The organic light-emitting device described above may also include at least one layer selected from a hole injection layer, a hole transport layer, an electron blocking layer, an emission layer, a hole blocking layer, an electron transport layer and an electron injection layer. These organic layers may have double-layered structures.

An organic light-emitting device according to embodiments of the present invention may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. An organic light-emitting device according other embodiments may have a first electrode/single layer having both hole injection and hole transport capabilities/emission layer/electron transport layer/second electrode structure, or a first electrode/single layer having both hole injection and hole transport capabilities/emission layer/electron transport layer/electron injection layer/second electrode structure. An organic light-emitting device according yet other embodiments may have a first electrode/hole injection layer/hole transport layer/emission layer/single layer having both electron transport and electron injection capabilities/second electrode structure, or a first electrode/single layer having both hole injection and hole transport capabilities/emission layer/single layer having both electron transport and electron injection capabilities/second electrode structure.

An organic light-emitting device according to embodiments of the present invention may have various structures, such as a top emission type organic light-emitting device structure or a bottom emission type organic light-emitting device structure.

According to embodiments of the present invention, a method of manufacturing an organic light-emitting device is provided. FIG. 1 illustrates the structure of an organic light-emitting device according to an embodiment of the present invention. Referring to FIG. 1, the organic light-emitting device includes a substrate, a first electrode (anode), a hole injection layer (HIL), a hole transport layer (HTL), an emission layer (EML), an electron transport layer (ETL), an electron injection layer (EIL), and a second electrode (cathode).

The first electrode is formed on the substrate by deposition or sputtering. The first electrode may be formed of a first electrode material having a high work function. The first electrode may be an anode or a cathode. The substrate may be any substrate conventionally used in organic light-emitting devices, and may be, for example, a glass substrate or a transparent plastic substrate having good mechanical strength, thermal stability, transparency, surface planarity, handling convenience, and water resistance. The first electrode material may include at least one material selected from indium tin oxide (ITO), indium zinc oxide (IZO), tin oxide ($SnO_2$), zinc oxide (ZnO), aluminum (Al), silver (Ag), and magnesium (Mg), which have good conductivity, and may form a transparent or reflective electrode.

A HIL may be formed on the first electrode by vacuum deposition, spin coating, casting, Langmuir Blodgett (LB) deposition, or the like. When the HIL is formed by vacuum deposition, the vacuum deposition conditions may vary according to the compound used to form the HIL and the desired structure and thermal properties of the HIL to be formed. In general, however, the vacuum deposition may be performed at a deposition temperature of about 100° C. to about 500° C., under a pressure of about $10^{-8}$ torr to about $10^{-3}$ torr, at a deposition speed of about 0.01 to about 100 Å/sec, and to a layer thickness of about 10 Å to about 5 µm.

When the HIL is formed by spin coating, the coating conditions may vary according to the compound used to form the HIL and the desired structure and thermal properties of the HIL to be formed. In general, however, the coating speed may be about 2000 rpm to about 5000 rpm, and the temperature for heat treatment (performed to remove the solvent after coating) may be about 80° C. to about 200° C.

Any known HIL material may be used. Nonlimiting examples of HIL materials include to form the HIL. Nonlimiting examples of HIL materials include phthalocyanine compounds (such as copper phthalocyanine), star-burst type amine derivatives (such as TCTA, 4,4',4"-tris(3-methylphenylphenylamino)triphenylamine (m-MTDATA), N,N'-di(1-naphthyl)-N,N'-diphenylbenzidine) (NPB), TDATA, and 2-TNATA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and (polyaniline)/poly(4-styrenesulfonate) (PANT/PSS).

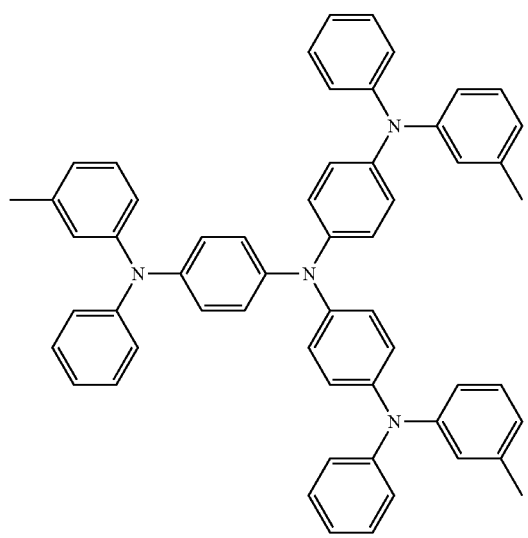

m-MTDATA

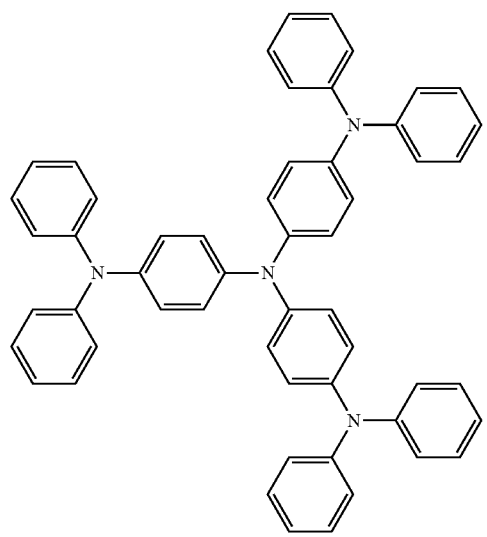

TDATA

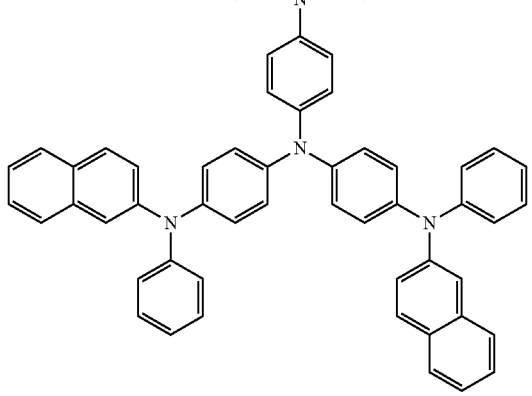

2-TNATA

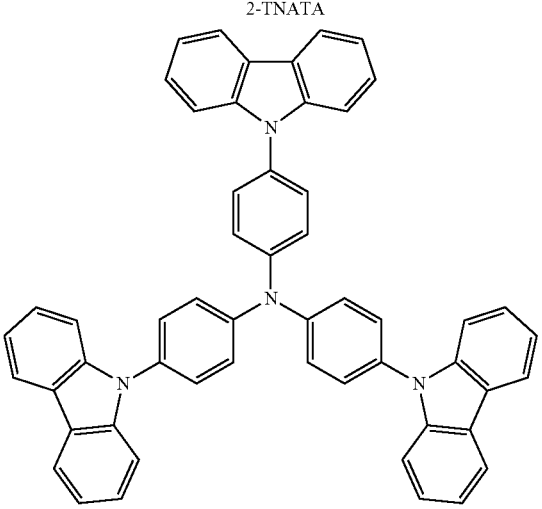

TCTA

The thickness of the HIL may be about 100 to about 10,000 Å. In some embodiments, for example, the thickness of the HIL is about 100 to about 1,000 Å. When the HIL has a thickness within these ranges, the HIL has good hole injection characteristics without increasing driving voltage.

A HTL may be formed on the HIL by vacuum deposition, spin coating, casting, LB deposition, or the like. When the HTL is formed by vacuum deposition or spin coating, the conditions for deposition and coating are similar to those for the formation of the HIL, although the conditions for the deposition and coating may vary according to the material used to form the HTL.

The HTL may be formed of any known material used to form a HTL. Nonlimiting examples of suitable materials for the HTL include carbazole derivatives (such as N-phenylcarbazole and polyvinylcarbazole), and typical amine derivatives having an aromatic condensation ring (such as 4,4'-bis[N-(1-naphthyl)-N-phenylamino]biphenyl (NPB), and N,N'-bis(3-methylphenyl)-N,N'-diphenyl-[1,1-biphenyl]-4,4'-diamine (TPD)).

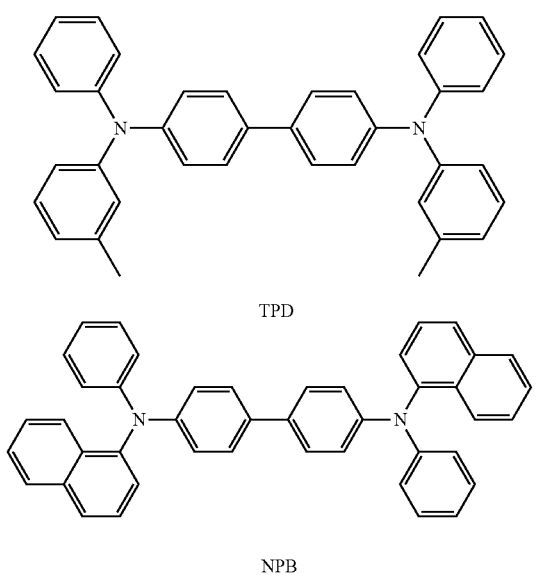

TPD

NPB

The thickness of the HTL may be about 50 to about 1,000 Å. In some embodiments, for example, the thickness of the HTL is about 100 to about 600 Å. When the HTL has a thickness within these ranges, the HTL has good hole transporting characteristics without substantially increasing driving voltage.

Optionally, an electron blocking layer may be formed on the HTL. The electron blocking layer blocks migration of electrons into the HTL. The electron blocking layer may include, for example, TATT represented by the following formula:

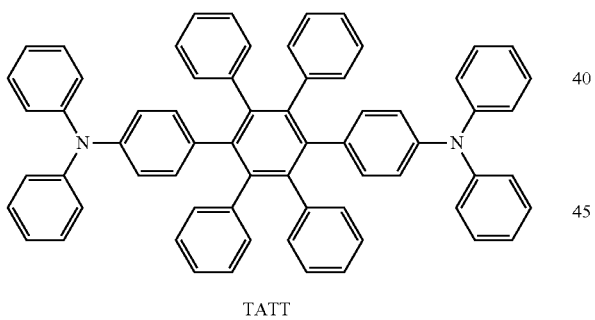

TATT

The thickness of the electron blocking layer may be about 50 to about 200 Å.

When the electron blocking layer has a thickness within this range, the electron blocking layer has good electron blocking characteristics without substantially increasing driving voltage.

The EML is formed on the resultant structure. The EML may be formed by vacuum deposition, spin coating, casting, or LB deposition. When the EML is formed by vacuum deposition or spin coating, the conditions for deposition and coating are similar to those for the formation of the HIL, although the conditions for deposition and coating may vary according to the material used to form the EML.

The EML may include the heterocyclic compound of Formula 1. The heterocyclic compound of Formula 1 may be used as a host of the EML. Alternatively, when the heterocyclic compound of Formula 1 is used to form the EIL or the ETL, the EML of the organic light-emitting device may be formed of any suitable light-emitting material for forming the EML of an organic light-emitting device. Nonlimiting examples of suitable light-emitting materials for forming the EML include known hosts and dopants. Dopants used to form the EML may include either a fluorescent dopant or a phosphorescent dopant.

Nonlimiting examples of hosts include $Alq_3$, 4,4'-N,N'-dicarbazole-biphenyl (CPB), poly(n-vinylcarbazole) (PVK), 9,10-di(naphthalene-2-yl)anthracene (ADN), distyrylarylene (DSA), arylamine and heteroarylamine compounds, anthracene compounds having symmetrical or asymmetrical structures, styrylanthracene compounds, pyrene compounds having symmetrical or asymmetrical structures, spirofluorene compounds, and fluorene compounds.

Either a fluorescent dopant or a phosphorescent dopant may be used as the dopant for forming the EML. Nonlimiting examples of the fluorescent dopant include styryl compounds, aryl and heterocyclic compounds, styryl heterocyclic compounds, and aminopyrene compounds. Nonlimiting examples of the phosphorescent dopant include $Ir(PPy)_3$ (PPy=phenylpyridine) (green), $F_2Irpic$, platinum(II) octaethylporphyrin (PtOEP), compound A represented by the following formula, RD 61 (which is a red phosphorescent dopant available from UDC), and metal-complex compounds including iridium (Ir), ruthenium (Ru), palladium (Pd), platinum (Pt), osmium (Os), or rhenium (Re) as a core metal.

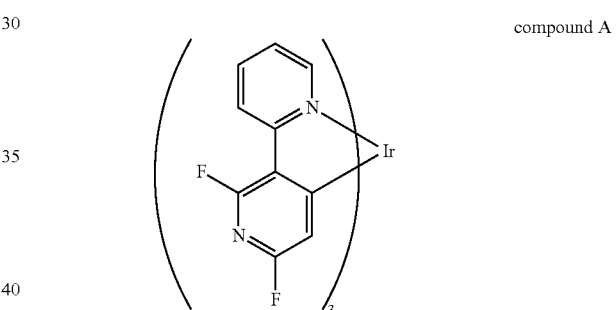

compound A

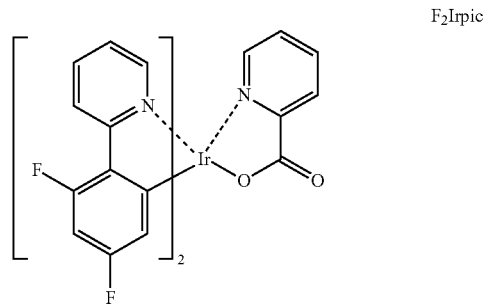

$F_2Irpic$

Nonlimiting examples of red dopants include platinum(II) octaethylporphyrin (PtOEP), $Ir(piq)_3$, $Btp_2Ir(acac)$, and DCJTB.

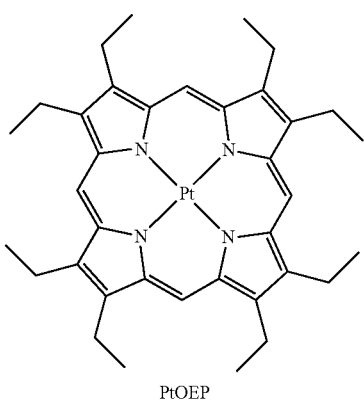

PtOEP

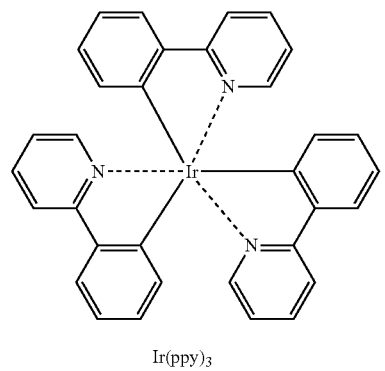

Ir(ppy)₃

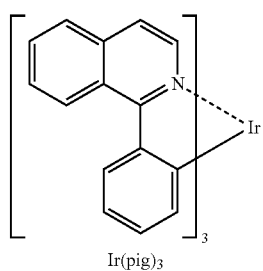

Ir(piq)₃

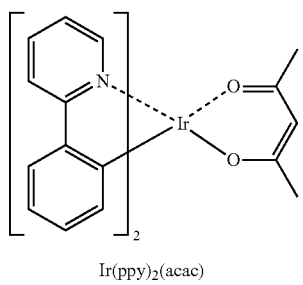

Ir(ppy)₂(acac)

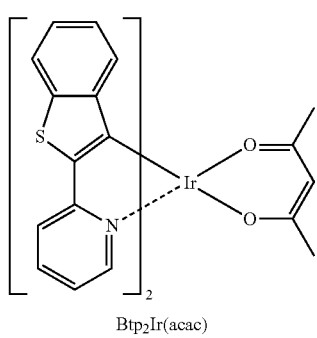

Btp₂Ir(acac)

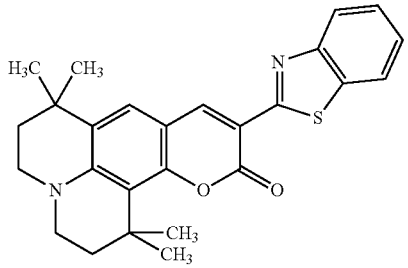

Ir(mpyp)₃

C545T

Nonlimiting examples of green dopants include Ir(ppy)₃ (where "ppy" denotes phenylpyridine), Ir(ppy)₂(acac), Ir(m-pyp)₃, and C545T.

Nonlimiting examples of blue dopants include F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl pherylene (TBPe), but are not limited thereto.

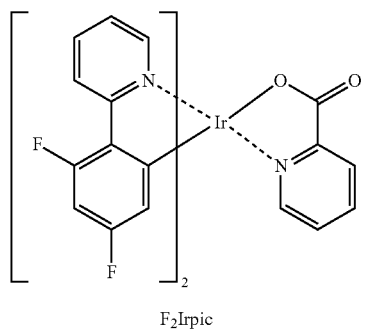
F₂Irpic
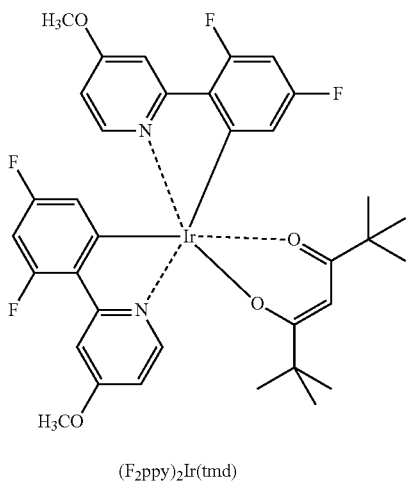
(F₂ppy)₂Ir(tmd)
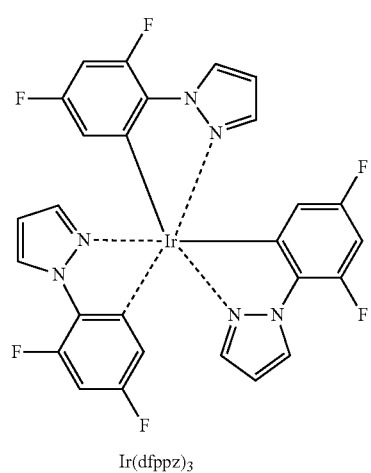
Ir(dfppz)₃
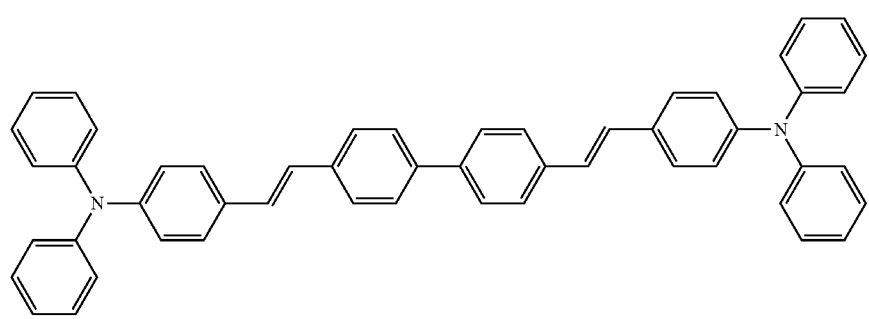
DPAVBi
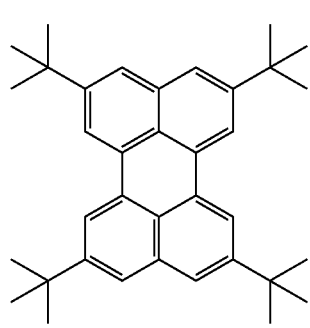
TBP The amount of the dopant may be about 0.1 to about 20 parts by weight based on 100 parts by weight of the EML material, which is the total weight of the host and dopant. In some embodiments, for example, the amount of the dopant is about 0.5 to about 12 parts by weight based on 100 parts by weight of the EML material. When the amount of the dopant is within these ranges, concentration quenching may be substantially prevented.

The thickness of the EML may be about 100 to about 1000 Å. In some embodiments, for example, the thickness of the EML is about 200 to about 600 Å. When the thickness of the EML is within these ranges, good light emission characteristics may be obtained without increasing driving voltage.

When the EML includes a phosphorescent dopant, a hole blocking layer (HBL, not shown in FIG. 1) may be formed on the EML in order to prevent diffusion of triplet excitons or holes into the ETL. The HBL may be formed of any suitable material without limitation. Nonlimiting examples of suitable materials for the HBL include oxadiazole derivatives, triazole derivatives, phenanthroline derivatives, bis(2-methyl-8-quinolato)-(p-phenylphenolato)-aluminum (Balq), bathocuproine (BCP), and tris(N-arylbenzimidazole) (TPBI).

The thickness of the HBL may be about 50 to about 1000 Å. In some embodiments, for example, the thickness of the HBL is about 100 to about 300 Å. When the thickness of the HBL is within these ranges, good hole-blocking characteristics may be obtained without increasing driving voltage.

The ETL may be formed on the HBL or EML by vacuum deposition, spin coating, or casting. When the ETL is formed by vacuum deposition or spin coating, the deposition and coating conditions may be similar to those for formation of the HIL, although the deposition and coating conditions may vary according to the compound used to form the ETL.

The ETL may be formed of any suitable material without limitation. Nonlimiting examples of suitable materials for the ETL include quinoline derivatives, for example, tris(8-quinolinorate)aluminum ($Alq_3$), TAZ, and Balq.

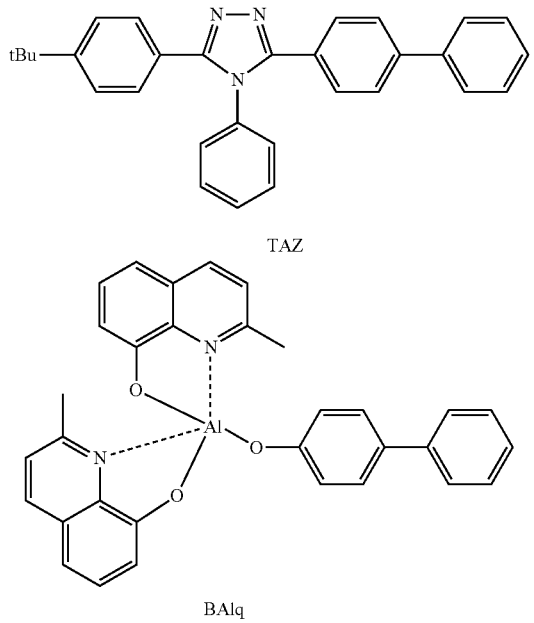

TAZ

BAlq

The thickness of the ETL may be about 100 to about 1000 Å. In some embodiments, for example, the thickness of the ETL is about 100 to about 500 Å. When the ETL has a thickness within these ranges, the ETL may have good electron transport characteristics without substantially increasing driving voltage.

In addition, an electron injection layer (EIL) for facilitating the injection of electrons from the cathode may be formed on the ETL. The EIL may be formed of the heterocyclic compound of Formula 1. Alternatively, the EIL may be formed of any suitable electron transport layer material. Nonlimiting examples of electron transport layer materials include $BaF_2$, LiF, NaCl, CsF, $Li_2O$, BaO, and Liq.

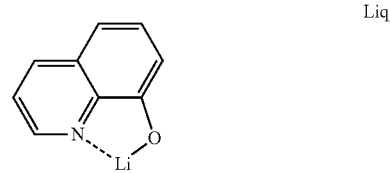

Liq

The deposition or coating conditions used to form the EIL may be similar to those used to form the HIL, although the deposition and coating conditions may vary according to the material used to form the EIL.

The thickness of the EIL may be about 1 to about 100 Å. In some embodiments, for example, the thickness of the EIL is about 5 to about 90 Å. When the EIL has a thickness within these ranges, the EIL may have good electron injection characteristics without substantially increasing driving voltage.

Finally, the second electrode may be formed on the EIL by vacuum deposition or sputtering. The second electrode may be a cathode or an anode. The material for forming the second electrode may be selected from metals, alloys, electrically conductive compounds, materials which have a low work function, and mixtures thereof. Nonlimiting examples of materials for the second electrode include lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission type organic light-emitting device, a transparent cathode formed of a transparent material such as ITO or IZO may be used as the second electrode.

The organic light-emitting device according to embodiments of the present invention may be included in various types of flat panel display devices, such as in passive matrix organic light-emitting display devices or active matrix organic light-emitting display devices. When the organic light-emitting device is included in an active matrix organic light-emitting display device including a thin-film transistor, the first electrode on the substrate may function as a pixel electrode, and be electrically connected to a source electrode or a drain electrode of the thin-film transistor. Moreover, the organic light-emitting device may also be included in a flat panel display device having a double-sided screen.

According to embodiments of the present invention, at least one layer of the organic light-emitting device may be formed of the heterocyclic compound of Formula 1 and can be formed using a deposition method or a wet method of coating a solution of the heterocyclic compound of Formula 1.

The following examples are presented for illustrative purposes only, and do not limit the scope of the present invention.

Synthesis Example 1

Synthesis of Compound 12

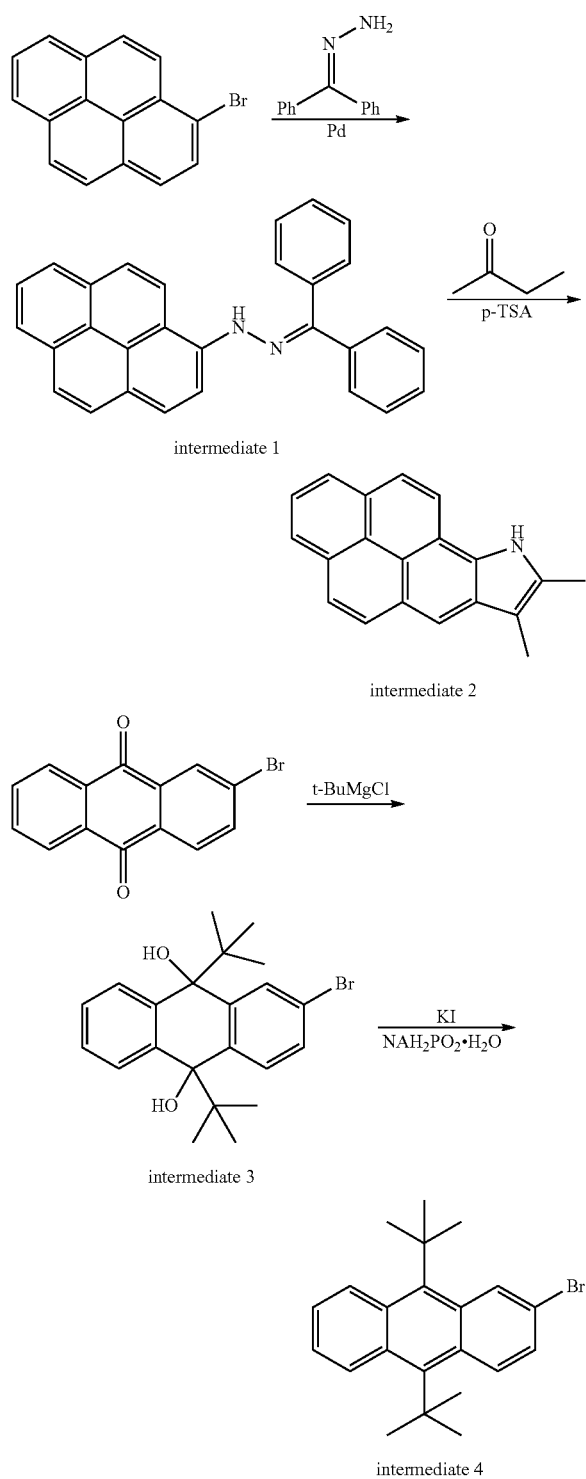

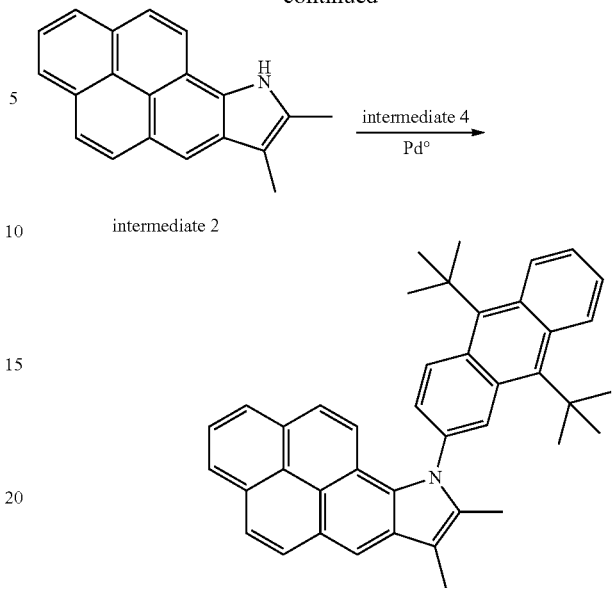

Synthesis of Intermediate 1

2.81 g (10 mmol) of 1-bromopyrene, 2.16 g (11 mmol) of benzophenone hydrazone, 1.44 g (15 mmol) of t-BuONa, 45 mg (0.2 mmol) of Pd(OAc)$_2$, and 82 g (0.2 mmol) of 2-dicyclohexylphosphino-2',4',6'-triisopropylbiphenyl were dissolved in 30 mL of toluene and stirred at 90° C. for 3 hours. The reaction product was cooled to room temperature. Distilled water was added thereto and the product was extracted twice with 80 mL of diethylether and once with 80 mL of dichloromethane. The organic layer was collected and dried using magnesium sulfate, followed by filtration. The solvent was evaporated, and the residue was separated and purified using silica gel column chromatography to obtain 3.37 g (yield: 85%) of Intermediate 1. This compound was identified using high-resolution mass spectroscopy (HR-MS). $C_{29}H_{20}N_2$ calc.: 396.1626. found 396.1630.

Synthesis of Intermediate 2

50 mL of methylethylketone was added to a mixture including 3.37 g (8.5 mmol) of Intermediate 1 and 3.2 g (17 mmol) of p-toluenesulfonic acid monohydrate and then the mixture was stirred at 110° C. for 24 hours. The reaction product was cooled to room temperature. Distilled water was added thereto and the product was extracted twice with 80 mL of diethylether and twice with 80 mL of dichloromethane. The organic layer was collected and dried using magnesium sulfate, followed by filtration. The solvent was evaporated, and the residue was separated and purified using silica gel column chromatography to obtain 1.7 g (yield: 75%) of Intermediate 2. This compound was identified using HR-MS. $C_{20}H_{15}N$ calc.: 269.1204. found 269.1208.

Synthesis of Intermediate 3

2.9 g (10 mmol) of 2-bromo-anthraquinone was dissolved in 50 mL of purified tetrahydrofuran under a nitrogen atmosphere. The reaction product was cooled to −78° C. and then 5 mL of $(CH_3)_3CMgCl$ (2.0M in diethylether) was slowly added thereto. The reaction product was stirred at −78° C. for 30 minutes and the temperature thereof was increased to room temperature by removing a cooler. The reaction product was stirred for one hour and was heated to 0° C. when the reaction was completed, and then 10 mL of an ammonium chloride aqueous solution was slowly added thereto. The reaction product was extracted twice with 40 mL of diethylether. The organic layer was collected and dried using magnesium sulfate, followed by filtration. The solvent was evaporated, and the residue was separated and purified using silica gel column chromatography to obtain 2.6 g (yield: 65%) of Intermediate 3. This compound was identified using HR-MS. $C_{22}H_{27}BrO_2$ calc.: 402.1194. found 402.1198.

Synthesis of Intermediate 4

A mixture of 2.6 g (6.47 mmol) of Intermediate 3, 10.7 g (64.7 mmol) of potassium iodide, and 11.4 g (129 mmol) of sodium hypophosphite hydrate was refluxed in a mixture of 600 mL of ortho-dichlorobenzene and 80 mL of acetic acid for 24 hours. The resulting product was cooled to room temperature and extracted with chloroform. Then the extracted product was dried with magnesium sulfate anhydride and was decompressed to evaporate the solvent. The residue was separated and purified using silica gel column chromatography to obtain 2.7 g (yield: 73%) of Intermediate 4. This compound was identified using HR-MS. $C_{22}H_{25}Br$ calc.: 368.1140. found 368.1144.

Synthesis of Compound 12

Under a nitrogen atmosphere, 1.88 g (7.0 mmol) of Intermediate 2, 3.1 g (8.4 mmol) of Intermediate 4, 2.0 g (21 mmol) of t-BuONa, 130 mg (0.14 mmol) of $Pd_2(dba)_3$, and 28 mg (0.14 mmol) of $P(t-Bu)_3$ were dissolved in 30 ml of toluene, and then the mixture was stirred at 90° C. for 3 hours. After the reaction was completed, the reaction product was cooled to room temperature and extracted three times with distilled water and 50 ml of diethylether. An organic layer was collected and dried using magnesium sulfate to evaporate the solvent. The residue was separated and purified using silica gel column chromatography to obtain 2.5 g (yield: 65%) of Compound 12. This compound was identified using HR-MS and nuclear magnetic resonance (NMR), $C_{42}H_{39}N$ calc.: 557.3082. found 557.3086; $^1H$ NMR (CDCl$_3$, 400 MHz) δ (ppm) 8.24 (s, 1H), 8.22 (s, 1H), 8.19-8.15 (m, 2H), 7.99-7.87 (m, 9H), 7.76 (qt, 2H), 7.71 (d, 1H), 7.63 (d, 1H), 7.52 (s, 1H), 7.49 (dd, 1H), 2.59 (s, 1H), 2.52 (s, 1H), 1.96 (s, 18H).

Synthesis Example 2

Synthesis of Compound 23

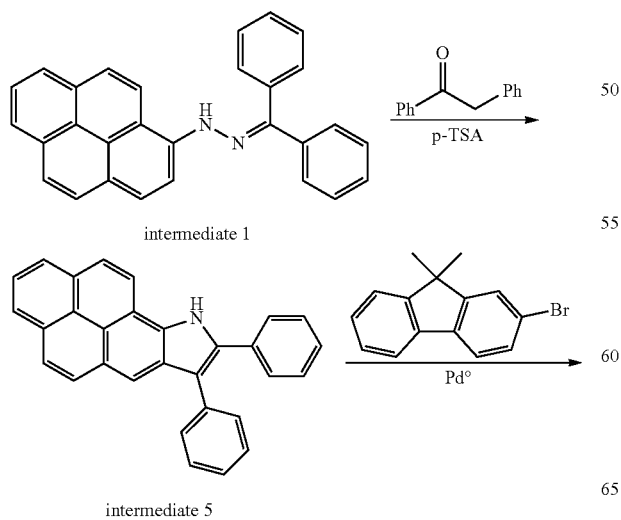

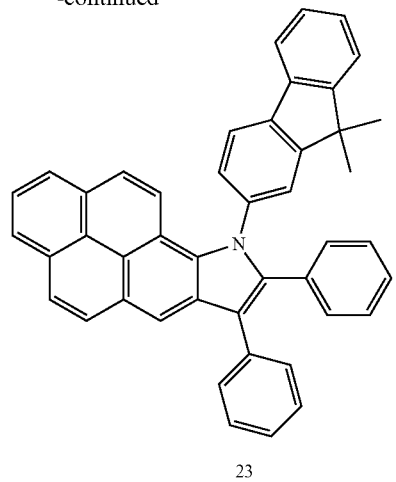

Synthesis of Intermediate 5

1.2 g (3.0 mmol) of Intermediate 1, 1.14 g (6.0 mmol) of p-toluenesulfonic acid monohydrate, and 1.2 g (6.0 mmol) of benzylphenylketone were dissolved in 16 mL of ethanol and 4 mL of toluene 80 mL and stirred at 110° C. for 24 hours. The reaction product was cooled to room temperature. Distilled water was added thereto and the product was extracted twice with 25 mL of diethylether and twice with 25 mL of dichloromethane. The organic layer was collected and dried using magnesium sulfate, followed by filtration. The solvent was evaporated, and the residue was separated and purified using silica gel column chromatography to obtain 0.86 g (yield: 73%) of Intermediate 5. This compound was identified using HR-MS. $C_{30}H_{19}N$ calc.: 393.1517. found 393.1521.

Synthesis of Compound 23

Compound 23 was synthesized with a yield of 68% in the same manner as Compound 12, except that Intermediate 5 was used instead of Intermediate 2 and 9,9'-dimethyl-2-boromofluorene was used instead of Intermediate 4. This compound was identified using HR-MS and NMR. $C_{45}H_{31}N$ calc.: 585.2456. found 585.2460; $^1H$ NMR (CDCl$_3$, 400 MHz) δ (ppm) 8.23 (d, 2H), 8.08 (d, 1H), 8.06 (d, 1H), 7.97 (t, 1H), 7.89 (dd, 2H), 7.80 (s, 1H), 7.63 (d, 1H), 7.55 (t, 3H), 7.49 (t, 3H), 7.41 (t, 2H), 7.35 (d, 2H), 7.31-7.21 (m, 3H), 6.95 (t, 1H). 6.84 (d, 1H), 6.76 (dd, 1H), 1.92 (s, 6H).

Synthesis Example 3

Synthesis of Compound 36

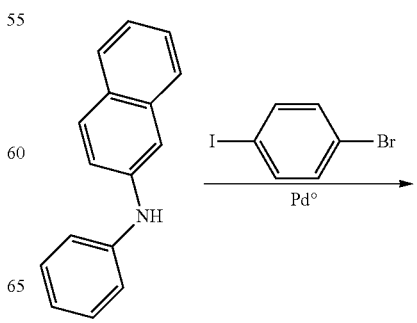

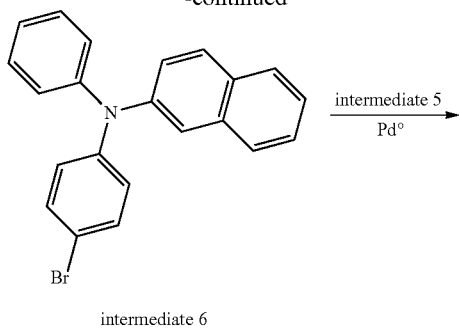

intermediate 6

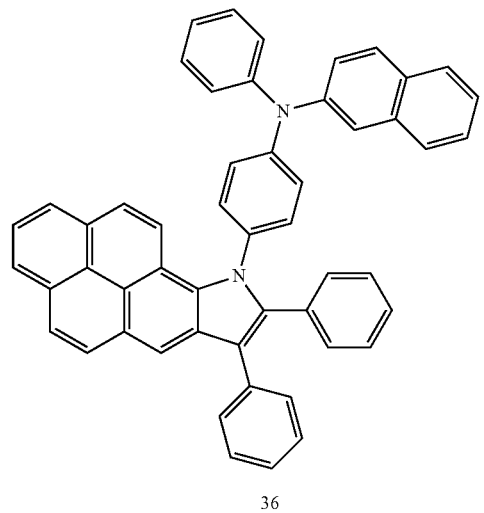

36

Synthesis of Intermediate 6

Under a nitrogen atmosphere, 1.10 g (5.0 mmol) of N-phenyl-2-naphthylamine, 1.56 g (5.5 mmol) of 1-bromo-4-iodobenzene, 1.4 g (15 mmol) of t-BuONa, 91 mg (0.10 mmol) of $Pd_2(dba)_3$, and 20 mg (0.10 mmol) of $P(t-Bu)_3$ were dissolved in 30 mL of toluene and stirred at 90° C. for 3 hours. After the reaction was completed, the reaction product was cooled to room temperature and extracted three times with distilled water and 50 ml of diethylether. The organic layer was collected and dried using magnesium sulfate to evaporate the solvent. The residue was separated and purified using silica gel column chromatography to obtain 1.5 g (yield: 82%) of Intermediate 6. This compound was identified using HR-MS. $C_{22}H_{16}BrN$ calc.: 373.0466. found 373.0470.

Synthesis of Compound 36

Compound 36 was synthesized with a yield of 62% in the same manner as Compound 12, except that Intermediate 5 was used instead of Intermediate 2 and Intermediate 6 was used instead of Intermediate 4. This compound was identified using HR-MS and NMR. $C_{52}H_{34}N_2$ calc.: 686.2722. found 686.2726; $^1H$ NMR ($CDCl_3$, 400 MHz) δ (ppm) 8.23 (d, 1H), 8.05 (dd, 2H), 7.98 (t, 1H), 7.90 (dd, 2H), 7.80 (s, 1H), 7.72-7.61 (m, 3H), 7.59-7.46 (m, 5H), 7.45-7.24 (m, 13H), 7.13 (dd, 1H), 6.62 (t, 1H), 6.46 (d, 2H), 6.38 (d, 2H).

Synthesis Example 4

Synthesis of Compound 39

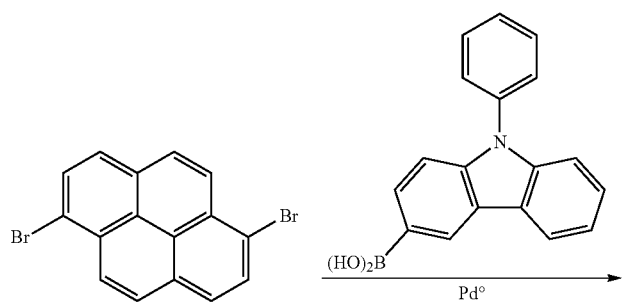

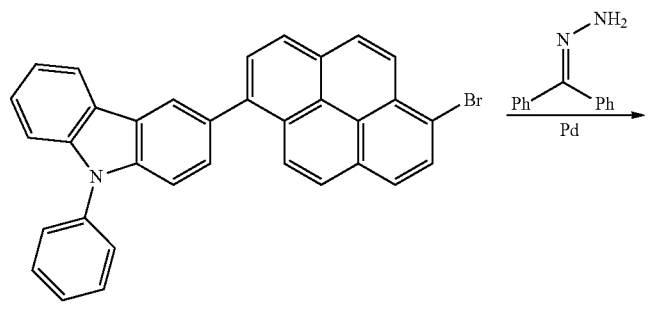

intermediate 7

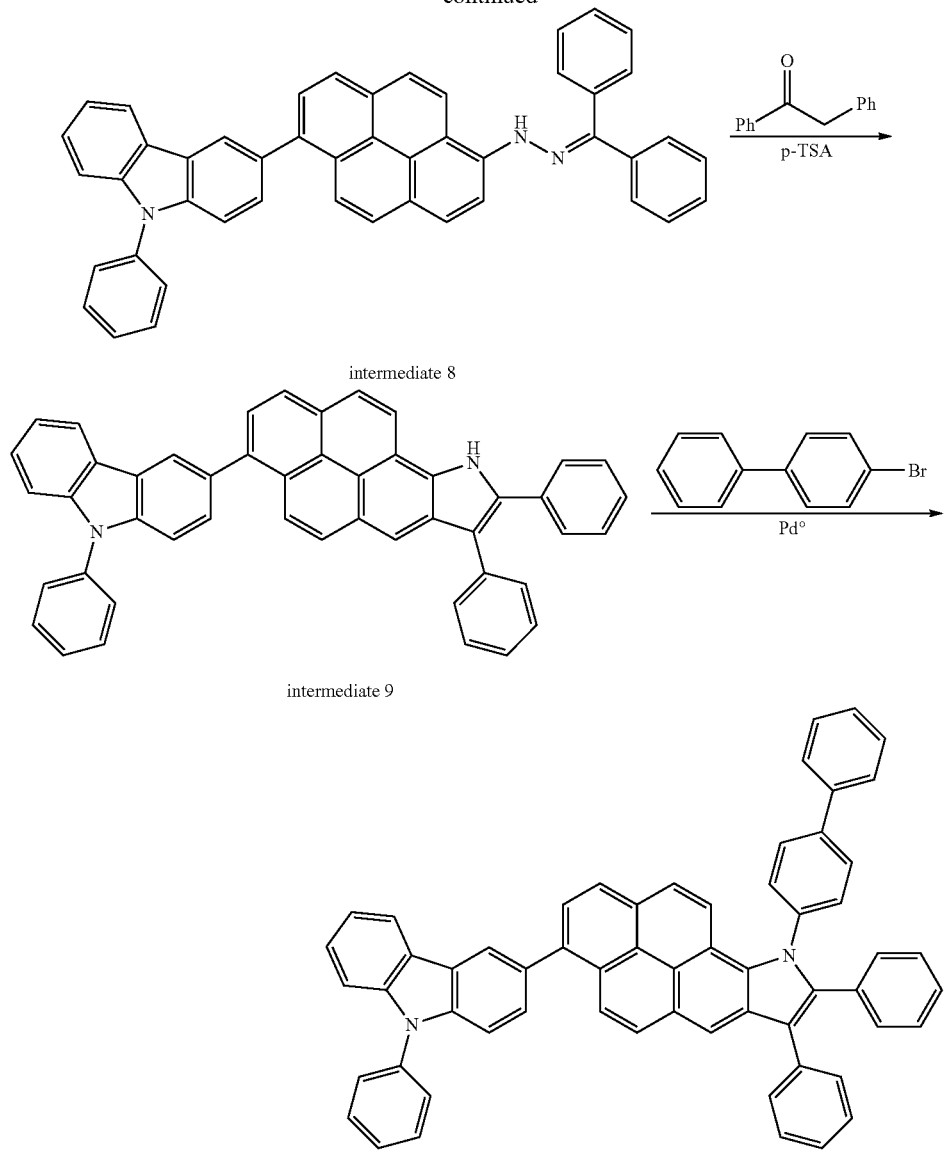

Synthesis of Intermediate 7

7.2 g (20 mmol) of 1,6-dibromopyrene, 2.87 g (10 mmol) of 9-phenylcarbazole-3-boronic acid, 0.58 g (0.5 mmol) of Pd(PPh$_3$)$_4$, and 5.53 g (40 mmol) of K$_2$CO$_3$ were dissolved in 50 mL of a mixed solution THF/H$_2$O (2:1), and stirred at 80° C. for 5 hours. The reaction solution was extracted three times with 100 ml of diethylether. The organic layer was collected and dried using magnesium sulfate to evaporate the solvent. The residue was recrystallized with dichloromethane and normal hexane to obtain 3.8 g (yield: 73%) of Intermediate 7. This compound was identified using HR-MS. C$_{34}$H$_{20}$BrN calc.: 521.0779. found 521.0783.

Synthesis of Intermediate 8

Intermediate 8 was synthesized with a yield of 72% in the same manner as Intermediate 1, except that Intermediate 7 was used instead of 1-bromopyrene. This compound was identified using HR-MS. C$_{47}$H$_{31}$N$_3$ calc.: 637.2518. found 637.2522.

Synthesis of Intermediate 9

Intermediate 9 was synthesized with a yield of 76% in the same manner as Intermediate 5, except that Intermediate 8 was used instead of Intermediate 1. This compound was identified using HR-MS. C$_{48}$H$_{30}$N$_2$ calc.: 634.2409. found 634.2413.

Synthesis of Compound 39

Compound 39 was synthesized with a yield of 67% in the same manner as Compound 12, except that Intermediate 9 was used instead of Intermediate 2 and 4-bromobiphenyl was used instead of Intermediate 4. This compound was identified using HR-MS and NMR. C$_{60}$H$_{38}$N$_2$ calc.: 786.3035. found 786.3039; $^1$H NMR (CDCl$_3$, 400 MHz) δ (ppm) 8.15 (d, 1H), 8.06 (t, 1H), 8.02 (d, 1H), 7.94 (d, 1H), 7.84 (d, 1H), 7.73 (d, 1H), 7.59-7.51 (m, 4H), 7.49-7.45 (m, 4H), 7.43-7.24 (m, 21H), 7.07 (d, 1H), 6.89 (d, 2H).

Synthesis Example 5

Synthesis of Compound 49

Synthesis of Intermediate 10

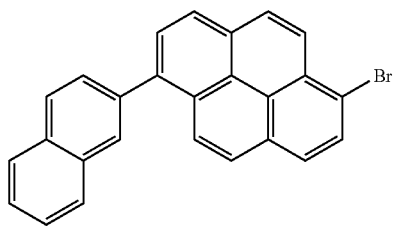 [SMILES: Brc1ccc2ccc3c(-c4ccc5ccccc5c4)ccc4ccc1c2c43]

Intermediate 10 was synthesized with a yield of 77% in the same manner as Intermediate 7, except that 2-naphthylboronic acid was used instead of 9-phenylcarbazole-boronic acid. $C_{26}H_{15}Br$ calc.: 406.0357. found 406.0361.

Synthesis of Intermediate 11

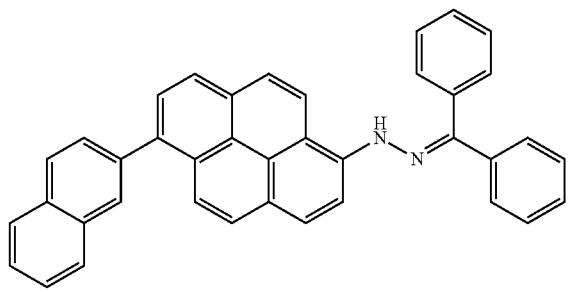 [SMILES: c1ccc(C(=NNc2ccc3ccc4c(-c5ccc6ccccc6c5)ccc5ccc2c3c54)c2ccccc2)cc1]

Intermediate 11 was synthesized with a yield of 62% in the same manner as Intermediate 1, except that Intermediate 10 was used instead of 1-bromopyrene. This compound was identified using HR-MS. $C_{39}H_{26}N_2$ calc.: 522.2096. found 522.2100.

Synthesis of Intermediate 12

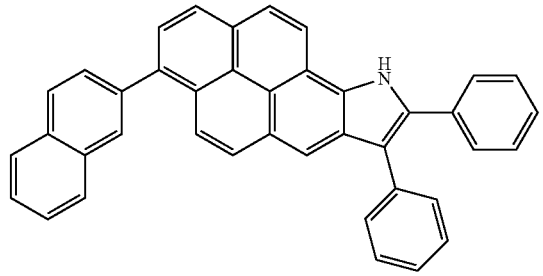 [SMILES: c1ccc(-c2[nH]c3c(cc4ccc5c(-c6ccc7ccccc7c6)ccc6ccc3c4c65)c2-c2ccccc2)cc1]

Intermediate 12 was synthesized with a yield of 70% in the same manner as Intermediate 5, except that Intermediate 11 was used instead of Intermediate 1. This compound was identified using HR-MS. $C_{40}H_{25}N$ calc.: 519.1987. found 519.1991.

Synthesis Example 6

Synthesis of Compound 49

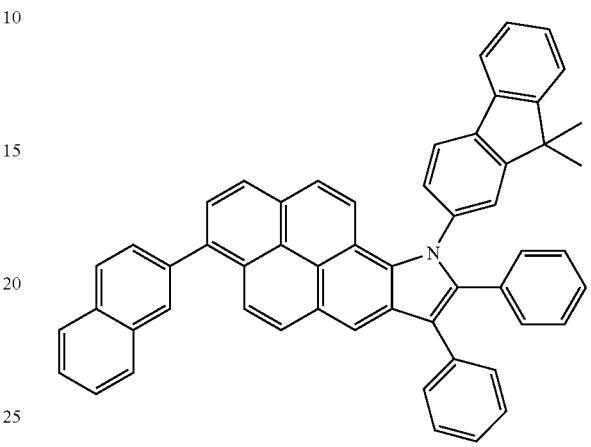

Compound 49 was synthesized with a yield of 66% in the same manner as Compound 12, except that Intermediate 12 was used instead of Intermediate 2 and 9,9'-dimethyl-2-bromofluorene was used instead of Intermediate 4. This compound was identified using HR-MS and NMR. $C_{55}H_{37}N$ calc.: 711.2926. found 711.2930; $^1H$ NMR (CDCl$_3$, 400 MHz) δ (ppm) 8.39 (dd, 1H), 8.05 (d, 1H), 7.98-7.89 (m, 4H), 7.75 (t, 2H), 7.61-7.51 (m, 4H), 7.49-7.46 (m, 2H), 7.44-7.24 (m, 15H), 6.96 (dd, 2H), 1.96 (s, 6H).

Synthesis Example 7

Synthesis of Compound 65

Synthesis of Intermediate 13

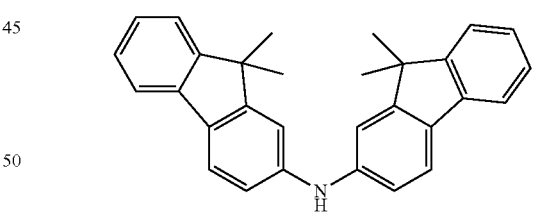

Under a nitrogen atmosphere, 1.91 g (7.0 mmol) of 9,9'-dimethyl-2-bromofluorene, 2.2 g (10.5 mmol) of 9,9'-dimethyl-2-aminofluorene, 2.0 g (21 mmol) of t-BuONa, 130 mg (0.14 mmol) of Pd$_2$(dba)$_3$, and 28 g (0.14 mmol) of P(t-Bu)$_3$ were dissolved in 30 ml of toluene, and then the mixture was stirred at 90° C. for 3 hours. After the reaction was completed, the reaction product was cooled to room temperature and extracted three times with distilled water and 50 ml of diethylether. The organic layer was collected and dried using magnesium sulfate to evaporate the solvent. The residue was separated and purified using silica gel column chromatography to obtain 1.7 g (yield: 61%) of Intermediate 13. This compound was identified using HR-MS. $C_{30}H_{27}N$ calc.: 401.2143. found 401.2147.

Synthesis of Intermediate 14

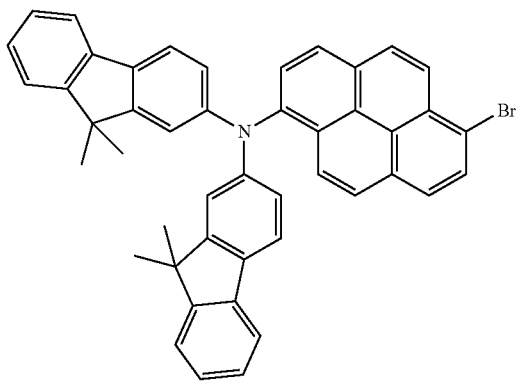 [SMILES: CC1(C)c2ccccc2-c2ccc(N(c3ccc4c(c3)C(C)(C)c3ccccc3-4)c3ccc4ccc5c(Br)ccc6ccc3c4c65)cc21]

Under a nitrogen atmosphere, 3.78 g (10.5 mmol) of 1,6-dibromopyrene, 2.8 g (7.0 mmol) of Intermediate 13, 2.0 g (21 mmol) of t-BuONa, 130 mg (0.14 mmol) of $Pd_2(dba)_3$, and 28 mg (0.14 mmol) of $P(t-Bu)_3$ were dissolved in 30 ml of toluene, and then the mixture was stirred at 90° C. for 3 hours. After the reaction was completed, the reaction product was cooled to room temperature and extracted three times with distilled water and 50 ml of diethylether. The organic layer was collected and dried using magnesium sulfate to evaporate the solvent. The residue was separated and purified using silica gel column chromatography to obtain 3.0 g (yield: 63%) of Compound 14. This compound was identified using HR-MS. $C_{46}H_{34}BrN$ calc.: 679.1875. found 679.1875.

Synthesis of Intermediate 15

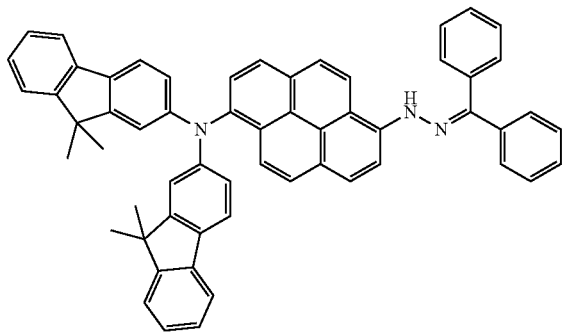 [SMILES: CC1(C)c2ccccc2-c2ccc(N(c3ccc4c(c3)C(C)(C)c3ccccc3-4)c3ccc4ccc5c(NN=C(c6ccccc6)c6ccccc6)ccc6ccc3c4c65)cc21]

Intermediate 15 was synthesized with a yield of 73% in the same manner as Intermediate 1, except that Intermediate 14 was used instead of 1-bromopyrene. This compound was identified using HR-MS. $C_{59}H_{45}N_3$ calc.: 795.3613. found 795.3618.

Synthesis of Intermediate 16

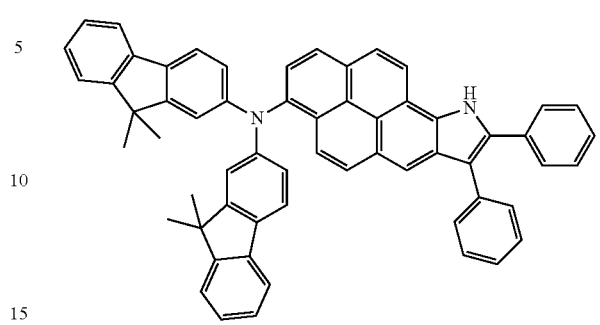

Intermediate 16 was synthesized with a yield of 76% in the same manner as Intermediate 5, except that Intermediate 15 was used instead of Intermediate 1. This compound was identified using HR-MS. $C_{60}H_{44}N_2$ calc.: 792.3504. found 792.3508.

Synthesis Example 8

Synthesis of Compound 65

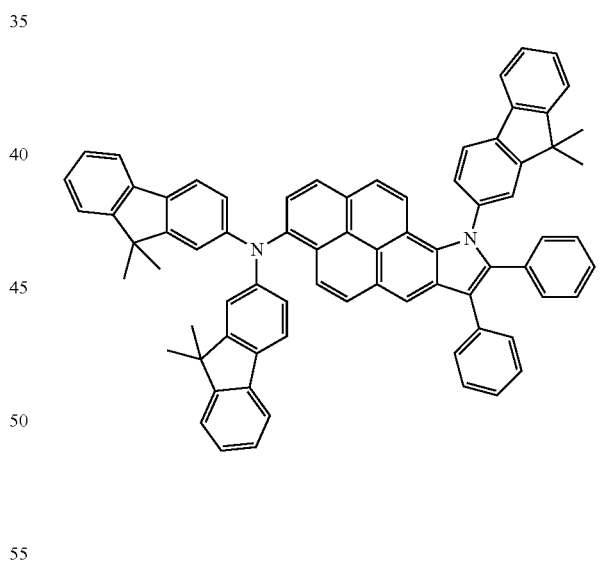

Compound 65 was synthesized with a yield of 71% in the same manner as Compound 12, except that Intermediate 16 was used instead of Intermediate 2 and 9,9'-dimethyl-bromofluorene was used instead of Intermediate 4. This compound was identified using HR-MS and NMR. $C_{75}H_{56}N_2$ calc.: 984.4443. found 984.4447; $^1H$ NMR (CDCl$_3$, 400 MHz) δ (ppm) 8.23 (d, 1H), 7.99-7.90 (m, 4H), 7.81 (d, 1H), 7.70-7.65 (m, 3H), 7.59-7.52 (m, 4H), 7.49-7.46 (m, 2H), 7.43-7.20 (m, 14H), 7.10 (d, 2H), 7.04 (d, 1H), 6.95 (t, 2H), 6.89 (d, 2H), 6.68 (dd, 2H), 2.03 (s, 12H), 1.96 (s, 6H).

Synthesis Example 9

Synthesis of Compound 67

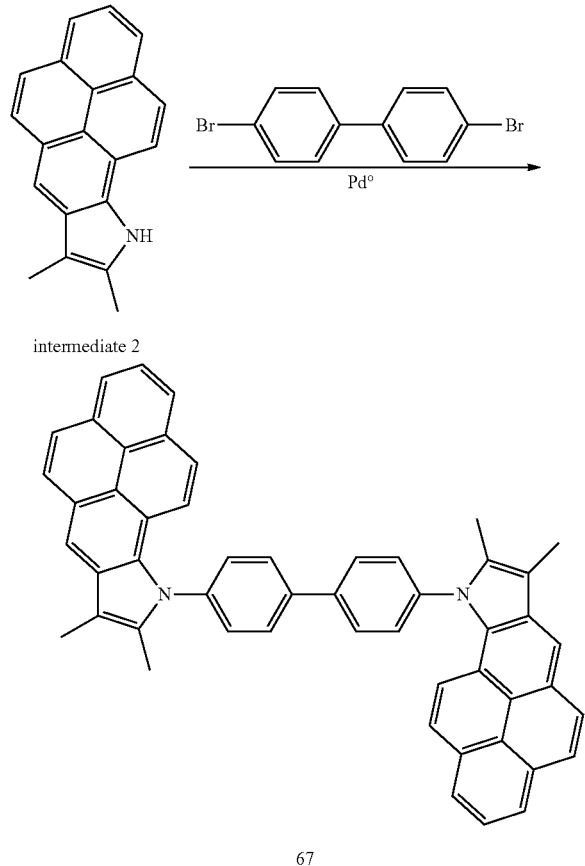

intermediate 2

67

510 mg (1.3 mmol) of Intermediate 2, 190 mg (0.6 mmol) of 4,4'-dibromobiphenyl, 180 mg (1.8 mmol) of t-BuONa, 20 mg (0.02 mmol) of Pd$_2$(dba)$_3$, and 9.5 mg (0.02 mmol) of 2-dicyclohexylphosphino-2',4',6'-triisopropylbiphenyl were dissolved in 15 mL of toluene and stirred at 90° C. for 3 hours. After the reaction was completed, the reaction product was cooled to room temperature and extracted three times with distilled water and 30 ml of diethylether. The organic layer was collected and dried using magnesium sulfate to evaporate the solvent. The residue was separated and purified using silica gel column chromatography to obtain 240 mg (yield: 57%) of Compound 67. This compound was identified using HR-MS and nuclear magnetic resonance (NMR). $C_{52}H_{36}N_2$ calc.: 688.2878. found 688.2882; $^1$H NMR (CDCl$_3$, 400 MHz) δ (ppm) 8.23 (d, 4H), 8.01-7.89 (m, 10H), 7.26-7.21 (m, 6H), 6.24 (dd, 4H), 2.29 (s, 6H), 2.22 (s, 6H).

Example 1

An anode was prepared by cutting a Corning 15 Ωcm$^2$ (1200 Å) ITO glass substrate to a size of 50 mm×50 mm×0.7 mm, ultrasonically cleaning the glass substrate using isopropyl alcohol and pure water for 5 minutes each, and then irradiating with UV light for 30 minutes and exposing to ozone to clean. Then, the anode was mounted in a vacuum deposition apparatus.

2-TNATA, was vacuum-deposited on the anode to a thickness of 600 Å to form an HIL, and 4,4'-bis[N-(1-naphthyl)-N-phenylamino]biphenyl (NPB) was vacuum-deposited on the HIL to a thickness of 300 Å to form a HTL.

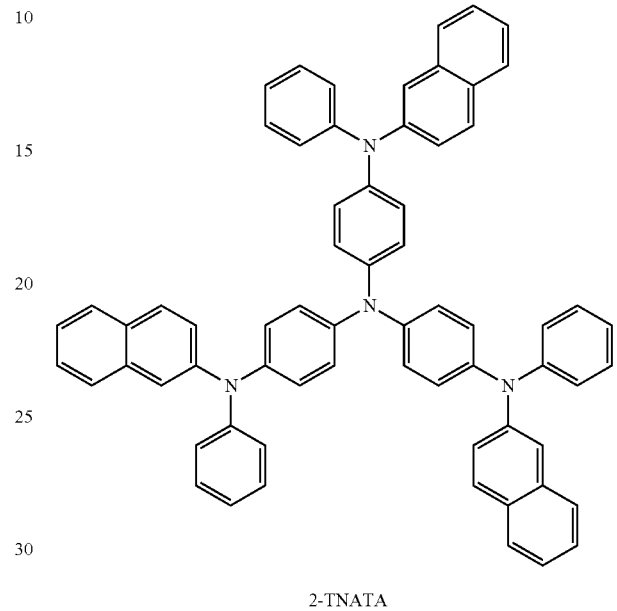

2-TNATA 9,10-di-naphthalene-2-yl-anthracene (DNA) as a blue fluorescent host and Compound 12 as a blue fluorescent dopant were co-deposited at a weight ratio of 98:2 on the HTL to form an EML having a thickness of 300 Å.

Next, Alq$_3$ was deposited on the EML to a thickness of 300 Å to form an ETL, and LiF was deposited on the ETL to a thickness of 10 Å to form an EIL. Finally, Al was vacuum-deposited on the EIL to a thickness of 3000 Å to form a LiF/Al electrode (cathode), thereby completing the manufacture of an organic light-emitting device.

Example 2

An organic light-emitting device was manufactured in the same manner as Example 1, except that Compound 23 was used instead of Compound 12 to form the EML.

Example 3

An organic light-emitting device was manufactured in the same manner as Example 1, except that Compound 36 was used instead of Compound 12 to form the EML.

Example 4

An organic light-emitting device was manufactured in the same manner as Example 1, except that Compound 39 was used instead of Compound 12 to form the EML.

Example 5

An organic light-emitting device was manufactured in the same manner as Example 1, except that Compound 49 was used instead of Compound 12 to form the EML.

Example 6

An organic light-emitting device was manufactured in the same manner as Example 1, except that Compound 65 was used instead of Compound 12 to form the EML.

Example 7

An organic light-emitting device was manufactured in the same manner as Example 1, except that Compound 67 was used instead of Compound 1 to form the EML.

Comparative Example 1

An organic light-emitting device was manufactured in the same manner as Example 1, except that 1,4-bis-(2,2-diphenylvinyl)biphenyl (DPVBi) was used as a blue fluorescent dopant instead of Compound 12 to form the EML.

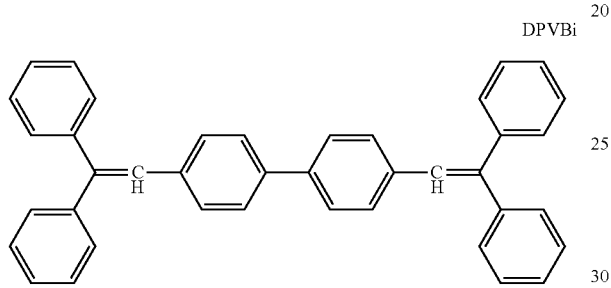

DPVBi

The driving voltage, luminance, color coordinates, and luminescent efficiency of each of the organic light-emitting devices of Examples 1 through 7 and Comparative Example 1 were measured at a current density of 50 mA/cm². The results are shown in Table 1 below.

TABLE 1

|  | Light-emitting material | Driving voltage (V) | Current density (mA/cm²) | Luminance (cd/m²) | Luminescent efficiency (cd/A) | Emission color | Half life-span (hr@ 100 mA/cm²) |
|---|---|---|---|---|---|---|---|
| Example 1 | Compound 12 | 6.30 | 50 | 3,258 | 6.52 | blue | 256 hr |
| Example 2 | Compound 23 | 6.18 | 50 | 3,398 | 6.80 | blue | 273 hr |
| Example 3 | Compound 36 | 6.08 | 50 | 3,110 | 6.22 | blue | 228 hr |
| Example 4 | Compound 39 | 6.41 | 50 | 3,520 | 7.04 | blue | 275 hr |
| Example 5 | Compound 49 | 6.12 | 50 | 3.815 | 7.63 | blue | 295 hr |
| Example 6 | Compound 65 | 6.04 | 50 | 3,684 | 7.37 | blue | 268 hr |
| Example 7 | Compound 67 | 6.16 | 50 | 3,496 | 6.99 | blue | 249 hr |
| Comparative Example 1 | DPVBi | 7.85 | 50 | 1,560 | 3.12 | blue | 113 hr |

Referring to Table 1, the organic light-emitting devices including the heterocyclic compounds of Formula 1 according to embodiments of the present invention had better driving voltage characteristics than the device including DPVBi. Thus, the devices including the heterocyclic compounds of Formula 1 had higher luminescent efficiency and good I-V-L characteristics. In particular, lifetime characteristics were markedly improved in the organic light-emitting devices according to Examples 1 through 7, as compared to the organic light-emitting device according to Comparative Example 1.

The heterocyclic compounds of Formula 1 have high Tgs or high melting points, and thus have high heat resistance against Joule's heat generated between an organic layer and a metallic electrode when light emission occurs. The heterocyclic compounds of Formula 1 also have high durability in high-temperature environments, good electrical characteristics, and high charge transporting capabilities. Thus, the heterocyclic compounds of Formula 1 may be used as at least one of an electron injecting material, an electron transporting material, and a material for emission layers, where these materials are suitable for any color fluorescent and phosphorescent devices, such as red, green, blue, and white fluorescent and phosphorescent devices.

Organic light-emitting devices including organic layers containing the heterocyclic compounds of Formula 1 have high durability when stored or operated, and have high efficiency, low driving voltages, and high luminance.

While the present invention has been illustrated and described with reference to certain exemplary embodiments, it is understood by those of ordinary skill in the art that various modifications and changes may be made to the described embodiments without departing from the spirit and scope of the present invention as defined by the following claims.

What is claimed is:

1. A heterocyclic compound comprising a compound represented by Formula 1 below:

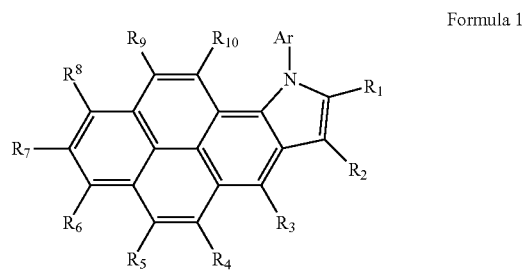

Formula 1 wherein:

Ar is selected from the group consisting of substituted and unsubstituted $C_6$-$C_{60}$ aryl groups, substituted and unsubstituted $C_4$-$C_{60}$ heteroaryl groups, amino groups substituted with at least one substituted or unsubstituted $C_5$-$C_{50}$ aryl group, and substituted and unsubstituted $C_6$-$C_{60}$ condensed polycyclic groups;

each of $R_3$ through $R_{10}$ is independently selected from the group consisting of hydrogen atoms, heavy hydrogen atoms, substituted and unsubstituted $C_1$-$C_{50}$ alkyl groups, substituted and unsubstituted $C_1$-$C_{50}$ alkoxy groups, substituted and unsubstituted $C_1$-$C_{50}$ alkoxycarbonyl groups, substituted and unsubstituted $C_6$-$C_{60}$ aryl groups, substituted and unsubstituted $C_5$-$C_{50}$ aryloxy groups, substituted and unsubstituted $C_5$-$C_{50}$ arylthio groups, amino groups substituted with at least one substituted or unsubstituted $C_5$-$C_{50}$ aryl group, substituted and unsubstituted $C_3$-$C_{50}$ carbon rings, substituted and unsubstituted $C_4$-$C_{60}$ heteroaryl groups, substituted and unsubstituted $C_4$-$C_{60}$ heterocyclic groups, substituted and unsubstituted $C_6$-$C_{60}$ condensed polycyclic groups, halogen atoms, cyano groups, hydroxyl groups, and carboxyl groups;

$R_1$ is selected from the group consisting of heavy hydrogen atoms, substituted and unsubstituted $C_1$-$C_{50}$ alkyl groups, substituted and unsubstituted $C_1$-$C_{50}$ alkoxy groups, substituted and unsubstituted alkoxycarbonyl groups, substituted and unsubstituted $C_6$-$C_{60}$ aryl groups, substituted and unsubstituted $C_5$-$C_{50}$ aryloxy groups, substituted and unsubstituted $C_5$-$C_{50}$ arylthio groups, amino groups substituted with at least one substituted or unsubstituted $C_5$-$C_{50}$ aryl group, substituted and unsubstituted $C_3$-$C_{50}$ carbon rings, substituted and unsubstituted $C_4$-$C_{60}$ heteroaryl groups, substituted and unsubstituted $C_4$-$C_{60}$ heterocyclic groups, substituted and unsubstituted $C_6$-$C_{60}$ condensed polycyclic groups, halogen atoms, cyano groups, hydroxyl groups, and carboxyl groups; and $R_2$ is methyl or phenyl.

2. The heterocyclic compound of claim 1, wherein Ar is selected from the group consisting of:
  unsubstituted monocyclic to tricyclic aryl groups selected from the group consisting of phenyl groups, naphthyl groups, biphenyl groups, terphenyl groups, fluorenyl groups, and carbazolyl groups, and
  monocyclic to tricyclic aryl groups substituted with one to three substituents selected from the group consisting of $C_1$-$C_5$ alkyl groups, $C_1$-$C_5$ alkoxy groups, cyano groups, amino groups, phenoxy groups, phenyl groups, and halogen atoms.

3. The heterocyclic compound of claim 1, wherein:
each of $R_3$ through $R_{10}$ is selected from the group consisting of:
  hydrogen atoms,
  heavy hydrogen atoms,
  methyl groups,
  unsubstituted monocyclic to tricyclic aryl groups selected from the group consisting of phenyl groups, naphthyl groups, biphenyl groups, terphenyl groups, fluorenyl groups, and carbazolyl groups,
  monocyclic to tricyclic aryl groups substituted with one to three substituents selected from the group consisting of $C_1$-$C_5$ alkyl groups, $C_1$-$C_5$ alkoxy groups, cyano groups, $C_1$-$C_5$ alkyl phenoxy groups, phenyl groups, halogen atoms, and —N(R')(R'') groups wherein each of R' and R'' is independently selected from the group consisting of hydrogen atoms, $C_1$-$C_{20}$ alkyl groups, $C_6$-$C_{20}$ aryl groups, and $C_3$-$C_{20}$ heteroaryl groups, and
  —N(R')(R'') groups wherein each of R' and R'' is independently selected from the group consisting of $C_6$-$C_{50}$ aryl groups and $C_3$-$C_{50}$ heteroaryl groups; and
$R_1$ is selected from the group consisting of:
  heavy hydrogen atoms,
  methyl groups,
  unsubstituted monocyclic to tricyclic aryl groups selected from the group consisting of phenyl groups, naphthyl groups, biphenyl groups, terphenyl groups, fluorenyl groups, and carbazolyl groups,
  monocyclic to tricyclic aryl groups substituted with one to three substituents selected from the group consisting of $C_1$-$C_5$ alkyl groups, $C_1$-$C_5$ alkoxy groups, cyano groups, $C_1$-$C_5$ alkyl phenoxy groups, phenyl groups, halogen atoms, and —N(R')(R'') groups wherein each of R' and R'' is independently selected from the group consisting of hydrogen atoms, $C_1$-$C_{20}$ alkyl groups, $C_6$-$C_{20}$ aryl groups, and $C_3$-$C_{20}$ heteroaryl groups, and
  —N(R')(R'') groups wherein each of R' and R'' is independently selected from the group consisting of $C_6$-$C_{50}$ aryl groups and $C_3$-$C_{50}$ heteroaryl groups.

4. The heterocyclic compound of claim 1, wherein the compound represented by Formula 1 comprises a compound selected from the group consisting of compounds represented by Formulae 2 through 5:

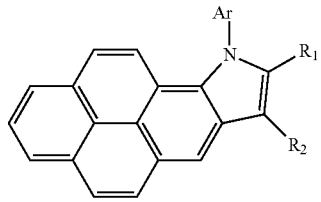

Formula 2

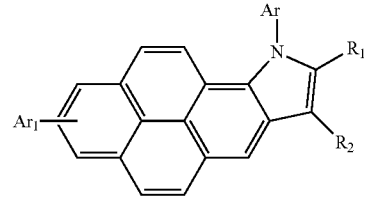

Formula 3

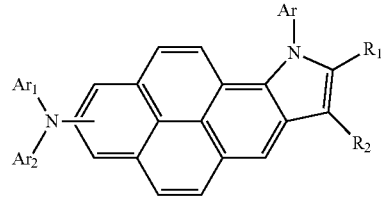

Formula 4

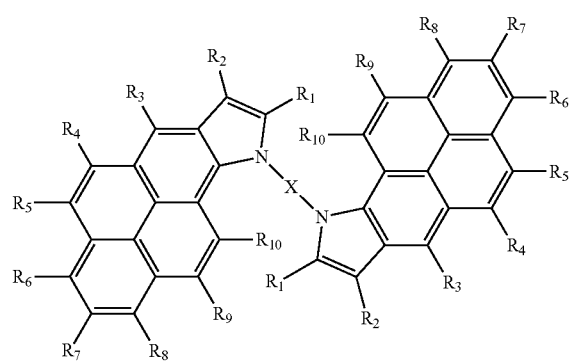

Formula 5 wherein:
  each of Ar, $Ar_1$, and $Ar_2$ is independently selected from the group consisting of substituted and unsubstituted $C_6$-$C_{60}$ aryl groups, substituted and unsubstituted $C_4$-$C_{60}$ heteroaryl groups, amino groups substituted with at least one substituted or unsubstituted $C_5$-$C_{50}$ aryl group, and substituted and unsubstituted $C_6$-$C_{60}$ condensed polycyclic groups;
  X is selected from the group consisting of substituted and unsubstituted $C_6$-$C_{30}$ arylene groups, substituted and unsubstituted $C_4$-$C_{30}$ heteroarylene groups, and substituted and unsubstituted $C_6$-$C_{30}$ condensed polycyclic groups;

each of $R_3$ through $R_{10}$ is independently selected from the group consisting of hydrogen atoms, heavy hydrogen atoms, substituted and unsubstituted $C_1$-$C_{50}$ alkyl groups, substituted and unsubstituted $C_1$-$C_{50}$ alkoxy groups, substituted and unsubstituted $C_1$-$C_{50}$ alkoxycarbonyl groups, substituted and unsubstituted $C_6$-$C_{60}$ aryl groups, substituted and unsubstituted $C_5$-$C_{50}$ aryloxy groups, substituted and unsubstituted $C_5$-$C_{50}$ arylthio groups, amino groups substituted with at least one substituted or unsubstituted $C_5$-$C_{50}$ aryl group, substituted and unsubstituted $C_3$-$C_{50}$ carbon rings, substituted and unsubstituted $C_4$-$C_{60}$ heteroaryl groups, substituted and unsubstituted $C_4$-$C_{60}$ heterocyclic groups, substituted and unsubstituted $C_6$-$C_{60}$ condensed polycyclic groups, halogen atoms, cyano groups, hydroxyl groups, and carboxyl groups; and $R_1$ is selected from the group consisting of heavy hydrogen atoms, substituted and unsubstituted $C_1$-$C_{50}$ alkyl groups, substituted and unsubstituted $C_1$-$C_{50}$ alkoxy groups, substituted and unsubstituted $C_1$-$C_{50}$ alkoxycarbonyl groups, substituted and unsubstituted $C_6$-$C_{60}$ aryl groups, substituted and unsubstituted $C_5$-$C_{50}$ aryloxy groups, substituted and unsubstituted $C_5$-$C_{50}$ arylthio groups, amino groups substituted with at least one substituted or unsubstituted $C_5$-$C_{50}$ aryl group, substituted and unsubstituted $C_3$-$C_{50}$ carbon rings, substituted and unsubstituted $C_4$-$C_{60}$ heteroaryl groups, substituted and unsubstituted $C_4$-$C_{60}$ heterocyclic groups, substituted and unsubstituted $C_6$-$C_{60}$ condensed polycyclic groups, halogen atoms, cyano groups, hydroxyl groups, and carboxyl groups.

5. The heterocyclic compound of claim 4, wherein, in Formulae 2 through 5, each of Ar, $Ar_1$, and $Ar_2$ is independently selected from the group consisting of:

unsubstituted monocyclic to tricyclic aryl groups selected from the group consisting of phenyl groups, naphthyl groups, biphenyl groups, terphenyl groups, fluorenyl groups, and carbazolyl groups, and monocyclic to tricyclic aryl groups substituted with one to three substituents selected from the group consisting of $C_1$-$C_5$ alkyl groups, $C_1$-$C_5$ alkoxy groups, cyano groups, amino groups, phenoxy groups, phenyl groups, and halogen atoms.

6. The heterocyclic compound of claim 4, wherein in Formulae 2 through 5:

each of $R_3$ through $R_{10}$ is selected from the group consisting of:
hydrogen atoms,
heavy hydrogen atoms,
methyl groups,
unsubstituted monocyclic to tricyclic aryl groups selected from the group consisting of phenyl groups, naphthyl groups, biphenyl groups, terphenyl groups, fluorenyl groups, and carbazolyl groups,
monocyclic to tricyclic aryl groups substituted with one to three substituents selected from the group consisting of $C_1$-$C_5$ alkyl groups, $C_1$-$C_5$ alkoxy groups, cyano groups, $C_1$-$C_5$ alkyl phenoxy groups, phenyl groups, halogen atoms, and —N(R')(R") groups wherein each of R' and R" is independently selected from the group consisting of hydrogen atoms, $C_1$-$C_{20}$ alkyl groups, $C_6$-$C_{20}$ aryl groups, and $C_3$-$C_{20}$ heteroaryl groups, and —N(R')(R") groups wherein each of R' and R" is independently selected from the group consisting of $C_6$-$C_{50}$ aryl groups and $C_3$-$C_{50}$ heteroaryl groups; and $R_1$ is selected from the group consisting of:
heavy hydrogen atoms,
methyl groups,
unsubstituted monocyclic to tricyclic aryl groups selected from the group consisting of phenyl groups, naphthyl groups, biphenyl groups, terphenyl groups, fluorenyl groups, and carbazolyl groups,
monocyclic to tricyclic aryl groups substituted with one to three substituents selected from the group consisting of $C_1$-$C_5$ alkyl groups, $C_1$-$C_5$ alkoxy groups, cyano groups, $C_1$-$C_5$ alkyl phenoxy groups, phenyl groups, halogen atoms, and —N(R')(R") groups wherein each of R' and R" is independently selected from the group consisting of hydrogen atoms, $C_1$-$C_{20}$ alkyl groups, $C_6$-$C_{20}$ aryl groups, and $C_3$-$C_{20}$ heteroaryl groups, and —N(R')(R") groups wherein each of R' and R" is independently selected from the group consisting of $C_6$-$C_{50}$ aryl groups and $C_3$-$C_{50}$ heteroaryl groups.

7. The heterocyclic compound of claim 4, wherein, in Formula 5, X is selected from the group consisting of phenylene groups, biphenylene groups, terphenylene groups, quaterphenylene groups, naphthylene groups, anthracenylene groups, phenanthrylene groups, chrysenylene groups, pyrenylene groups, perylenylene groups, fluorenylene groups, thiophenylene groups, 1-phenylthiophenylene groups, 1,4-diphenylthiophenylene groups, benzothiophenylene groups, 1-phenylbenzothiophenylene groups, 1,8-diphenylbenzothiophenylene groups, furylene groups, 1-phenyldibenzothiophenylene groups, 1,8-diphenylthiophenylene groups, dibenzofuranylene groups, 1-phenyldibenzofuranylene groups, 1,8-diphenyldibenzofuranylene groups, and benzothiazolylene groups.

8. The heterocyclic compound of claim 4, wherein, in Formulae 2 to 5, each of Ar, $Ar_1$, and $Ar_2$ is independently selected from the group consisting of:

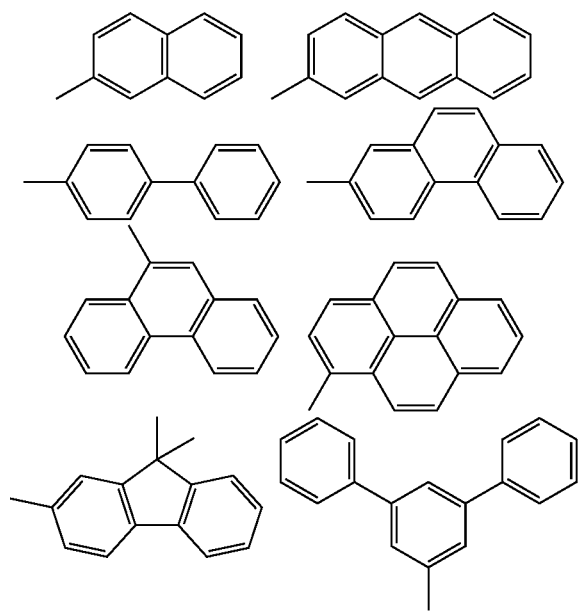

75
-continued
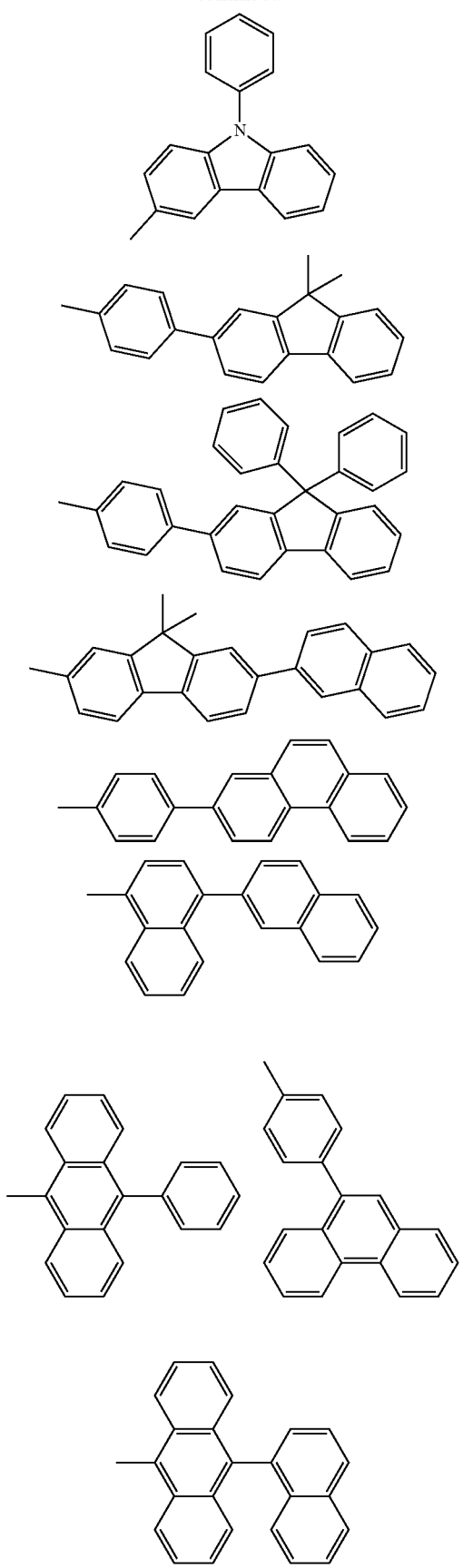
76
-continued
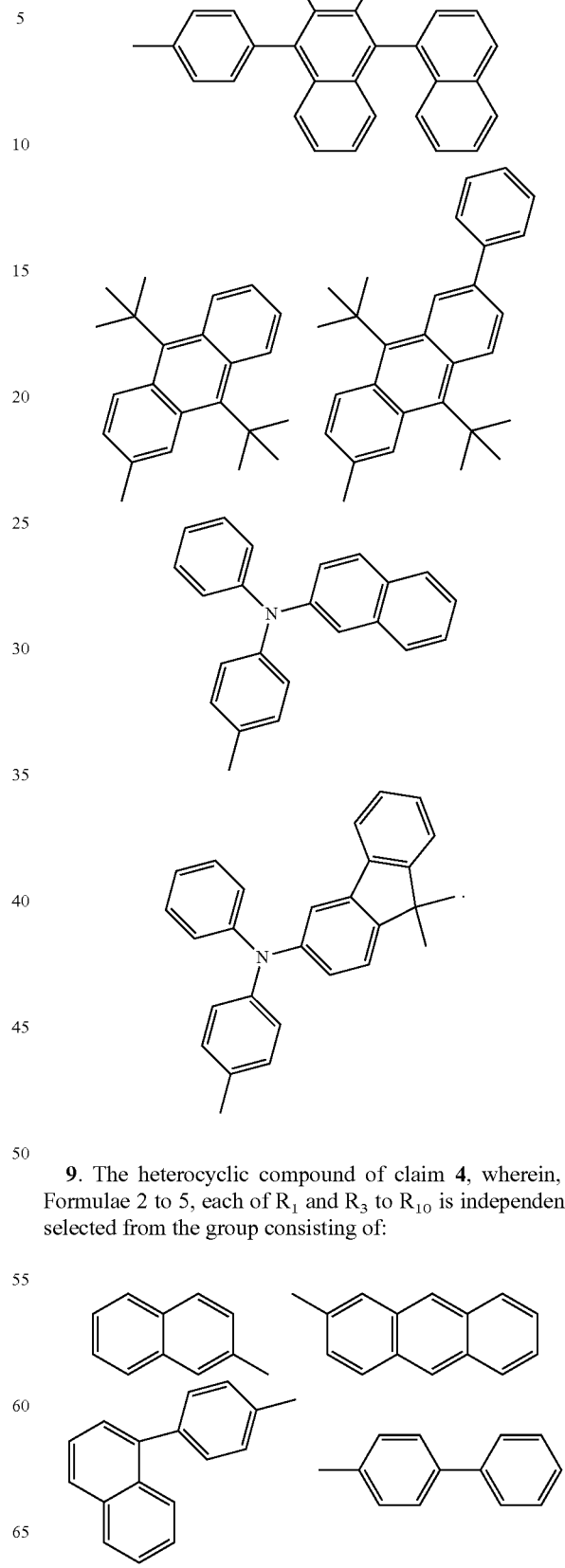
9. The heterocyclic compound of claim 4, wherein, in Formulae 2 to 5, each of $R_1$ and $R_3$ to $R_{10}$ is independently selected from the group consisting of:
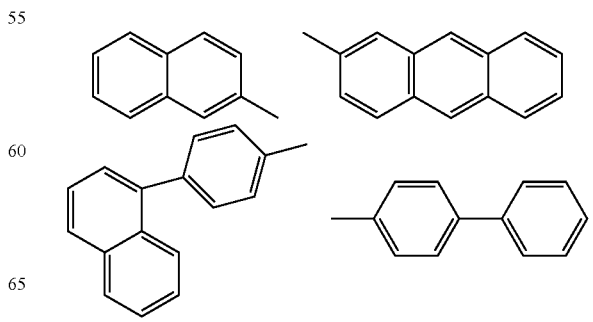

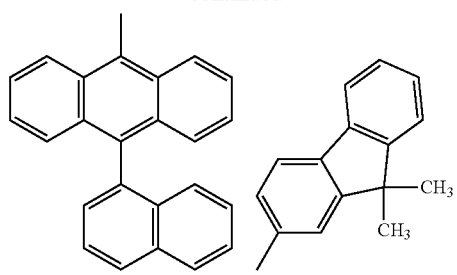
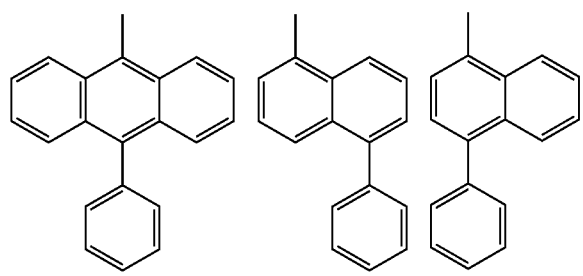
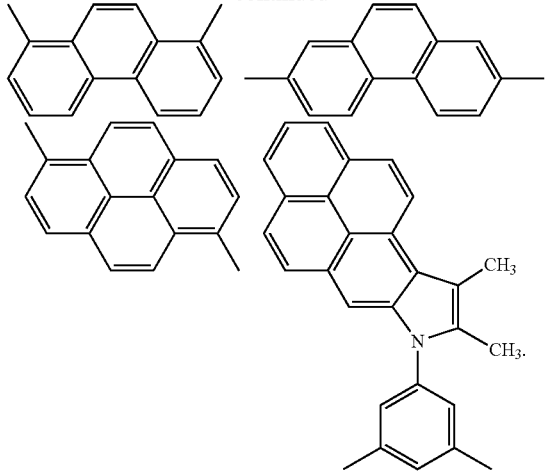
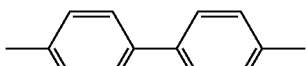
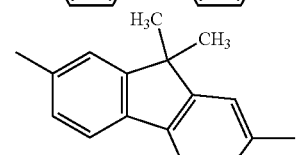
11. The heterocyclic compound of claim 1, wherein the compound represented by Formula 1 is selected from the group consisting of Compounds 12, 23, 36, 39, 49, 65 and 67:
12
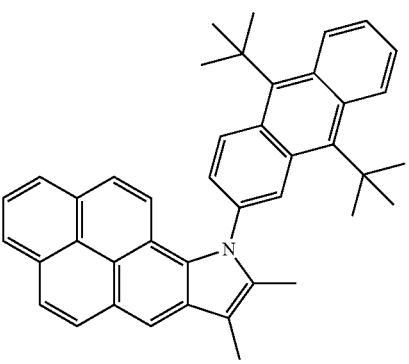
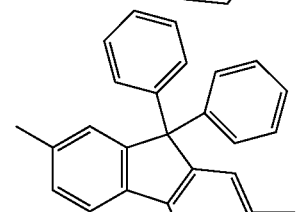
10. The heterocyclic compound of claim 4, wherein, in Formula 5, X is selected from the group consisting of:
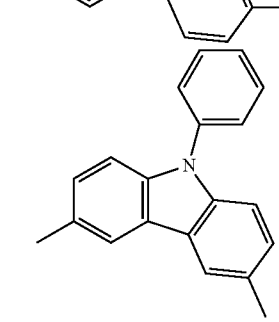
23
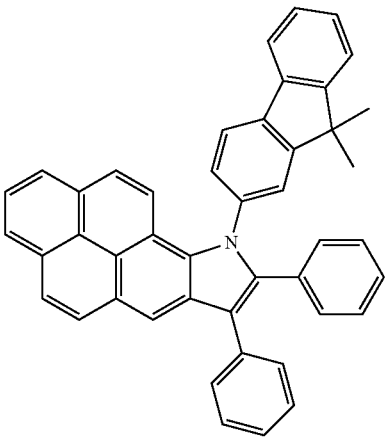

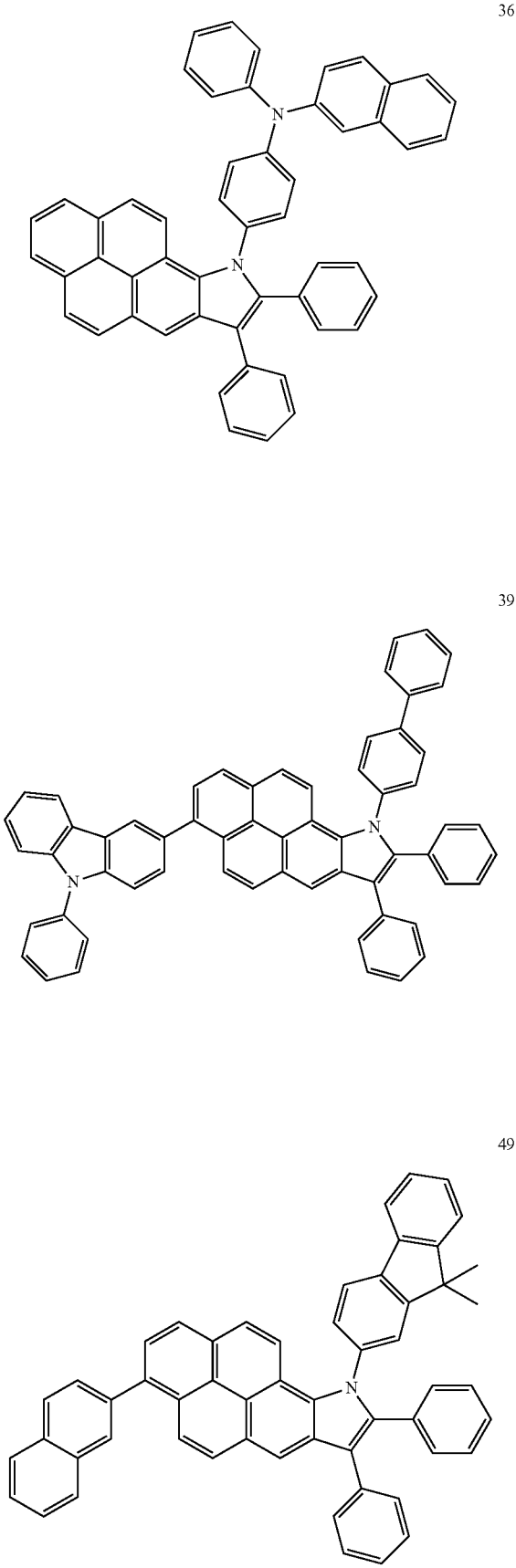

12. An organic light-emitting device comprising a first electrode, a second electrode, and an organic layer between the first electrode and the second electrode, wherein the organic layer comprises at least one organic layer comprising the heterocyclic compound of claim 1.

13. The organic light-emitting device of claim 12, wherein the at least one organic layer comprises an electron injection layer or an electron transport layer.

14. The organic light-emitting device of claim 12, wherein the at least one organic layer comprises an emission layer or a single layer having electron injecting capability and electron transporting capability.

15. The organic light-emitting device of claim 12, wherein the at least one organic layer comprises an emission layer comprising the heterocyclic compound of Formula 1 as a host for a fluorescent or phosphorescent device.

16. The organic light-emitting device of claim 12, wherein the at least one organic layer comprises an electron injection layer, an electron transport layer, and an emission layer, wherein the electron transport layer or the electron injection layer comprises the heterocyclic compound of Formula 1, and the emission layer comprises an anthracene compound or a $C_4$-$C_{50}$ heteroaryl compound or a styryl compound.

17. The organic light-emitting device of claim 12, wherein the at least one organic layer comprises an emission layer, an electron transport layer, and an electron injection layer, wherein the electron injection layer or the electron transport layer comprises the heterocyclic compound of Formula 1, and the emission layer comprises a red emission layer, a green emission layer, a blue emission layer, and a white emission layer, wherein at least one of the red emission layer, green emission layer, the blue emission layer and the white emission layer comprises a phosphorescent compound.

18. The organic light-emitting device of claim 12, wherein the at least one organic layer comprises at least one layer selected from the group consisting of a hole injection layer, a hole transport layer, an electron blocking layer, an emission layer, a hole blocking layer, an electron transport layer, and an electron injection layer.

19. The organic light-emitting device of claim 18, wherein the organic light-emitting device comprises a first electrode/hole injection layer/emission layer/second electrode structure, or a first electrode/hole injection layer/hole transport layer/emission layer/electron transport layer/second electrode structure, or a first electrode/hole injection layer/hole transport layer/emission layer/electron transport layer/electron injection layer/second electrode structure.

20. A flat panel display device comprising the organic light-emitting device according to claim 12, wherein the first electrode of the organic light-emitting device is electrically connected to a source electrode or a drain electrode of a thin film transistor.

21. An organic light-emitting device comprising a first electrode, a second electrode, and an organic layer between the first electrode and the second electrode, wherein the organic layer comprises at least one layer comprising the heterocyclic compound of claim 1, the at least one layer being formed using a wet process.

* * * * *

UNITED STATES PATENT AND TRADEMARK OFFICE
CERTIFICATE OF CORRECTION

PATENT NO. : 8,524,380 B2
APPLICATION NO. : 12/860817
DATED : September 3, 2013
INVENTOR(S) : Young-Kook Kim et al.

Page 1 of 1

It is certified that error appears in the above-identified patent and that said Letters Patent is hereby corrected as shown below:

In the Claims

Col. 71, line 12, Claim 1      Delete "unsubstituted alkoxycarbonyl",
Insert --unsubstituted $C_1$-$C_{50}$ alkoxycarbonyl--

Signed and Sealed this
Sixth Day of January, 2015

Michelle K. Lee
*Deputy Director of the United States Patent and Trademark Office*